(12) United States Patent
Arai et al.

(10) Patent No.: US 10,062,854 B2
(45) Date of Patent: Aug. 28, 2018

(54) ORGANIC MATERIAL AND PHOTOELECTRIC CONVERSION ELEMENT

(71) Applicants: Ryota Arai, Shuzuoka (JP); Takuma Yasuda, Fukuoka (JP); Woong Shin, Fukuoka (JP); Hideaki Komiyama, Fukuoka (JP); Yu Hidaka, Fukuoka (JP); Takahiro To, Fukuoka (JP); Seiichi Furukawa, Fukuoka (JP)

(72) Inventors: Ryota Arai, Shuzuoka (JP); Takuma Yasuda, Fukuoka (JP); Woong Shin, Fukuoka (JP); Hideaki Komiyama, Fukuoka (JP); Yu Hidaka, Fukuoka (JP); Takahiro To, Fukuoka (JP); Seiichi Furukawa, Fukuoka (JP)

(73) Assignees: RICOH COMPANY, LTD., Tokyo (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 37 days.

(21) Appl. No.: 15/596,423

(22) Filed: May 16, 2017

(65) Prior Publication Data

US 2017/0338424 A1 Nov. 23, 2017

(30) Foreign Application Priority Data

May 20, 2016 (JP) ................. 2016-101467

(51) Int. Cl.
*C07D 495/04* (2006.01)
*H01L 51/00* (2006.01)
*H01L 51/42* (2006.01)

(52) U.S. Cl.
CPC ........ *H01L 51/0074* (2013.01); *C07D 495/04* (2013.01); *H01L 51/0047* (2013.01); *H01L 51/0053* (2013.01); *H01L 51/0068* (2013.01); *H01L 51/42* (2013.01); *H01L 51/4253* (2013.01)

(58) Field of Classification Search
CPC .......................... C07D 495/14; H01L 51/0074
See application file for complete search history.

(56) References Cited

U.S. PATENT DOCUMENTS 9,246,110 B2 1/2016 Arai et al.
9,365,513 B2 6/2016 Yanagawa et al.
9,373,450 B2 6/2016 Arai et al.
9,378,899 B2 6/2016 Arai et al.
9,406,887 B2 8/2016 Arai et al.
2015/0041724 A1 2/2015 Arai et al.
2016/0260912 A1 9/2016 Arai et al.

FOREIGN PATENT DOCUMENTS

JP 2014-177409 9/2014
JP 2016-164128 9/2016

OTHER PUBLICATIONS

Chem. Mater. 2013, 25, 2274-2281.

*Primary Examiner* — Noble E Jarrell
*Assistant Examiner* — John S Kenyon
(74) *Attorney, Agent, or Firm* — Cooper & Dunham LLP

(57) ABSTRACT

To provide an organic material represented by General Formula (1) below:

General Formula (1)

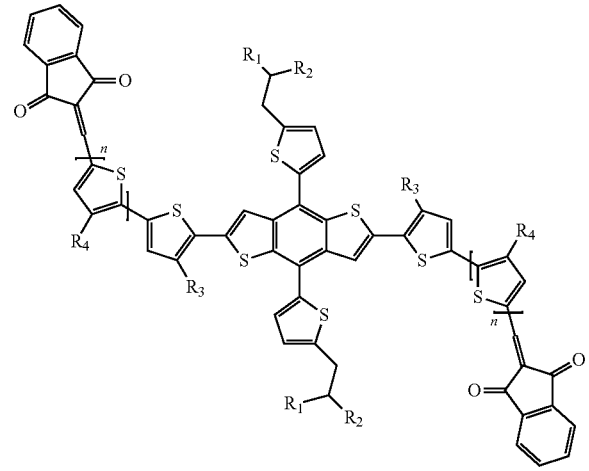

where, in General Formula (1), $R_1$ and $R_2$ are each independently an alkyl group having from 2 through 8 carbon atoms, $R_3$ and $R_4$ are each independently a straight-chain alkyl group having 1, 2, 4, 6, or 12 carbon atoms, or a hydrogen atom, and n is an integer of 1 or 2.

7 Claims, 2 Drawing Sheets

ORGANIC MATERIAL AND PHOTOELECTRIC CONVERSION ELEMENT

CROSS-REFERENCE TO RELATED APPLICATIONS

The present application claims priority under 35 U.S.C. § 119 to Japanese Patent Application No. 2016-101467 filed May 20, 2016. The contents of which are incorporated herein by reference in their entirety.

BACKGROUND OF THE INVENTION

Field of the Invention

The present disclosure relates to an organic material and a photoelectric conversion element.

Description of the Related Art

In recent years, the power for driving electric circuits has become extremely low. Preparing for the coming IoT society, various electronic parts, such as sensors, have been able to be driven with very low electric power (order of µW). As utilization of sensors, applications of the sensors for energy harvesting elements have been expected as self-sufficient energy supplies capable of generating and consuming power in-situ. Among the energy harvesting elements, photoelectric conversion elements have been attracted attentions as elements capable of generating power anywhere as long as there is light. As energy harvesting elements, particularly demanded are photoelectric conversion elements capable of efficiently generating electric power with indoor light, such as light of fluorescent lamps, and light of LED lamps.

It has been known that, as properties of a photoelectric conversion element, typically open-circuit voltage is largely reduced, when an amount of light is decreased. The above-described reduction in the open-circuit voltage is a major factor of deteriorating properties of a solar cell under weak light. The above-described tendency is also applied to known organic thin film solar cells. Therefore, an improvement of low open-circuit voltage under weak light is desired.

Moreover, it has been known that among the properties of the photoelectric conversion element, a short-circuit current density is proportional to an amount of light, when a light source is identical. The above-described tendency is also applied to so-called organic thin film solar cells. Know organic thin film solar cells have been developed with targeting sunlight as a light source. Among them, developments of p-type organic semiconductors have been particularly actively performed.

Meanwhile, photoelectric conversion elements targeting indoor light as a light source use light of fluorescent lamps or LED lamps as target light, not sunlight. Therefore, there is a need that photoelectric conversion elements exhibit high current values with light of fluorescent lamps or LED lamps. Since light from fluorescent lamps or LED lamps has a spectrum only in a visible light region, unlike sunlight, spectrum matching is low with a p-type organic semiconductor used for a known photoelectric conversion element targeting sunlight as a light source. Therefore, the photoelectric conversion element has a disadvantage that a current value is low with light from fluorescent lamps or LED lamps. Accordingly, there is a need for developing materials suitable for spectra of light from fluorescent lamps or LED lamps. Specifically, there is a need for a material having a shorter spectrum than an absorption spectrum of a p-type organic semiconductor targeting sunlight as a light source.

In "Chem. Mater. 2013, 25, 2274-2281," a material having relatively short absorption wavelength is disclosed, and an organic material exhibiting a relative high current value under pseudo sunlight is disclosed. However, properties of the material with low illuminance are not clearly described in "Chem. Mater. 2013, 25, 2274-2281."

Moreover, a film formation of a p-type organic semiconductor used for a bulk heterojunction organic thin film solar cell is performed by a solution coating process, and therefore the p-type organic semiconductor is desired to have high solubility. Particularly when it is desired to make a film thickness thick, and to sufficiently perform light absorption, higher solubility of the p-type organic semiconductor is desired. Moreover, a method for introducing an acceptor site into a low-molecular type p-type organic semiconductor is often used in order to adjust an absorption wavelength of the p-type organic semiconductor. In this case, solubility of the p-type organic semiconductor tends to be lowered, and there is a problem that the p-type organic semiconductor is not dissolved in a solvent used for film formation. Therefore, the above-described problem is solved by introducing a long-chain alkyl group into a skeleton of a p-type organic semiconductor. Also in "Chem. Mater. 2013, 25, 2274-2281," an acceptor site is introduced, and a long-chain alkyl group is introduced to secure solubility.

SUMMARY OF THE INVENTION

According to one aspect of the present disclosure, an organic material is represented by General Formula (1) below.

General Formula (1)

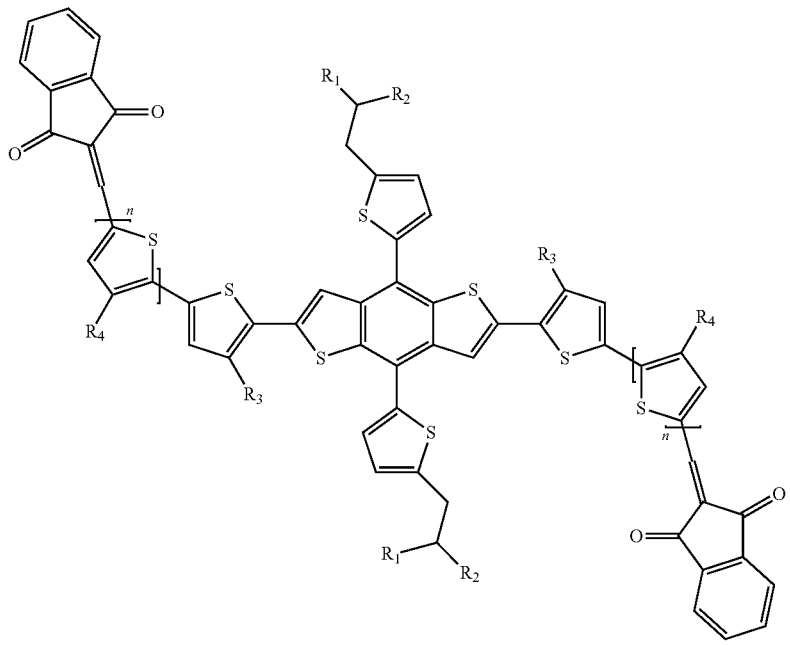

In General Formula (1), $R_1$ and $R_2$ are each independently an alkyl group having from 2 through 8 carbon atoms, $R_3$ and $R_4$ are each independently a straight-chain alkyl group having 1, 2, 4, 6, or 12 carbon atoms, or a hydrogen atom, and n is an integer of 1 or 2.

DESCRIPTION OF THE EMBODIMENTS

Figure 1:
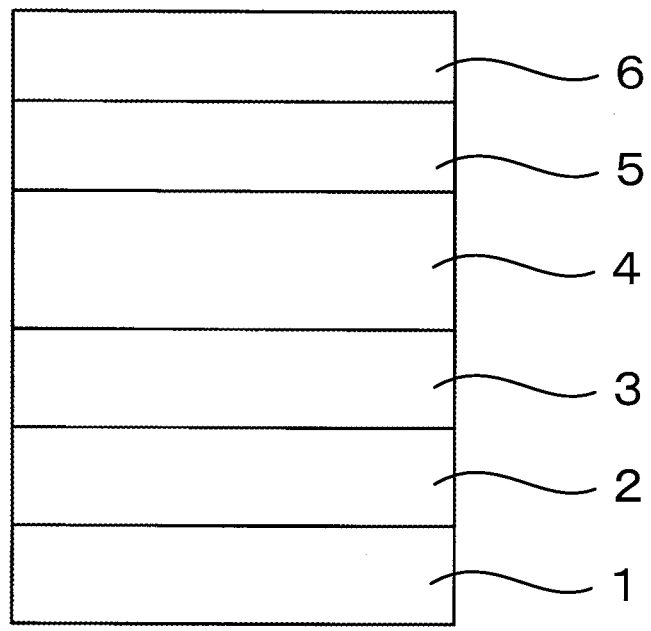
FIG. 1 is a schematic view illustrating one example of a structure of a photoelectric conversion element of the present disclosure.

An organic material and a photoelectric conversion element according to the present disclosure will be described below with reference to drawings.
Note that, the present disclosure is not limited to embodiments described below, and other embodiments, additions to the embodiments, and eliminations from the embodiments are also included in a scope of the present disclosure, as long as the above-mentioned changes are made within a scope at which a person skilled in the art can easily arrive, and any of the embodiments can exhibit functions and effects of the present disclosure.
In the present disclosure, the term "photoelectric conversion element" means an element which converts optical energy into electric energy, or an element which converts electric energy into optical energy. Specific examples of the photoelectric conversion element include solar cells and photo diodes.
The photoelectric conversion element will be described in detail below.

The photoelectric conversion element of the present disclosure has been accomplished based on finding below. Solubility of know organic materials in the art is not sufficient, and the organic materials cannot be formed into a thick layer. Moreover, it has been known that a bulk heterojunction organic thin film solar cell typically significantly reduce conversion efficiency, when the organic thin film solar cell is placed in an environment of high temperature. As a countermeasure, several means for improving heat resistance have been reported. However, improvements of heat resistance have not been yet sufficient. Particularly, properties of the organic thin film solar cell are more sensitive against heat under indoor light compared to the properties under sunlight, and therefore a further improvement of heat resistance is desired.

The present disclosure has an object to provide an organic material, which can realize a photoelectric conversion element that has high efficiency against very weak light, such as indoor light, and has high heat resistance.

An organic material of the present disclosure has high solubility. Since the organic material of the present disclosure is used, a photoelectric conversion element, which has high efficiency against very weak light, such as indoor lighting, and has high heat resistance, can be obtained.

<<Organic Material>>

The organic material of the present disclosure is represented by General Formula (1) below.

General Formula (1)

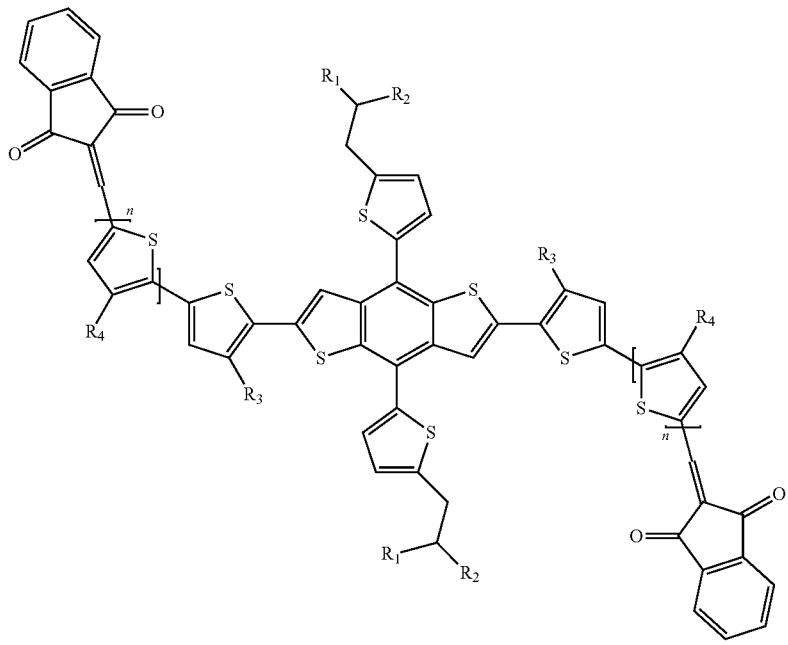

In General Formula (1), $R_1$ and $R_2$ are each independently an alkyl group having from 2 through 8 carbon atoms, $R_3$ and $R_4$ are each independently a straight-chain alkyl group having 1, 2, 4, 6, or 12 carbon atoms, or a hydrogen atom, and n is an integer of 1 or 2.

Examples of the organic material represented by General Formula (1) above include an organic material represented by General Formula (2) below and an organic material represented by General Formula (3).

General Formula (2)

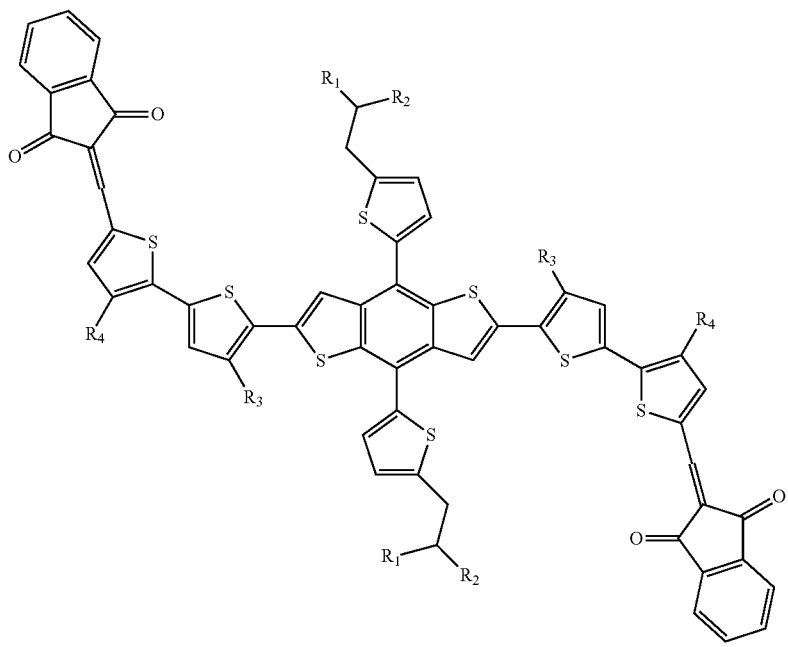

In General Formula (2), $R_1$ and $R_2$ are each independently an alkyl group having from 2 through 8 carbon atoms, and $R_3$ and $R_4$ are each independently a straight-chain alkyl group having 1, 2, 4, 6, or 12 carbon atoms, or a hydrogen atom.

General Formula (3)

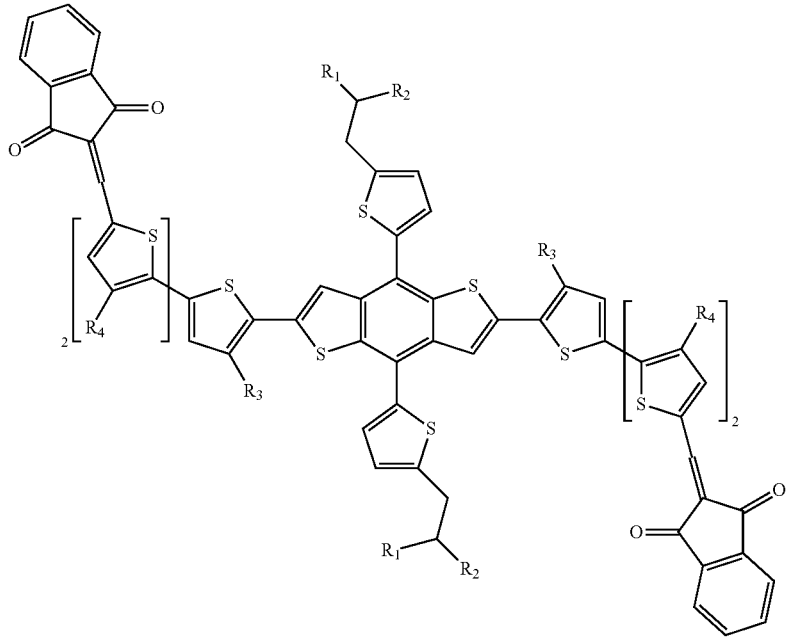

In General Formula (3), $R_1$ and $R_2$ are each independently an alkyl group having from 2 through 8 carbon atoms, and $R_3$ and $R_4$ are each independently a straight-chain alkyl group having 1, 2, 4, 6, or 12 carbon atoms, or a hydrogen atom.

$R_1$ and $R_2$ are each an alkyl group having from 2 through 8 carbon atoms. Examples of the alkyl group include an ethyl group, a butyl group, a hexyl group, and an octyl group. $R_1$ is preferably an ethyl group, and $R_2$ is preferably a hexyl group.

$R_3$ and $R_4$ are each independently a straight-chain alkyl group having 1, 2, 4, 6, or 12 carbon atoms, or a hydrogen atom. Examples of the alkyl group include a methyl group, an ethyl group, a butyl group, a hexyl group, and a dodecyl group. The alkyl group is preferably a hexyl group.

Particularly, it is important that a substituent of a thiophene group introduced into a benzene ring of benzodithiophene is a branched alkyl group via methylene. In "Chem. Mater. 2013, 25, 2274-2281" and SIPO Patent Publication No. CN-103788111, only a straight-chain alkyl group is disclosed as a substituent of a thiophene group introduced into a benzene ring of benzodithiophene. As described later, the different substituents above give different conversion efficiencies and heat resistance, and a material having a branched alkyl group for use in the present disclosure is more excellent in terms of conversion efficiency and heat resistance. A reason for it is not clear, but use of a branched alkyl group develops a phase separation structure required for a bulk heterojunction photoelectric conversion element, and form a structure suitable for charge separation and charge transportation.

In a bulk heterojunction, moreover, it has been known that stability of a structure of the bulk heterojunction is important for heat resistance. In the present disclosure, the alkyl chain is a branched chain, therefore, interaction between molecules is large because of entanglement of molecular chains, and therefore it is assumed that stability of the bulk heterojunction structure is improved when heat is applied.

Specific examples of the organic material represented by General Formula (1) include compounds represented by structural formulae below, but the present disclosure is not limited to the compounds represented by the structural formulae below.

Exemplary Compound 1
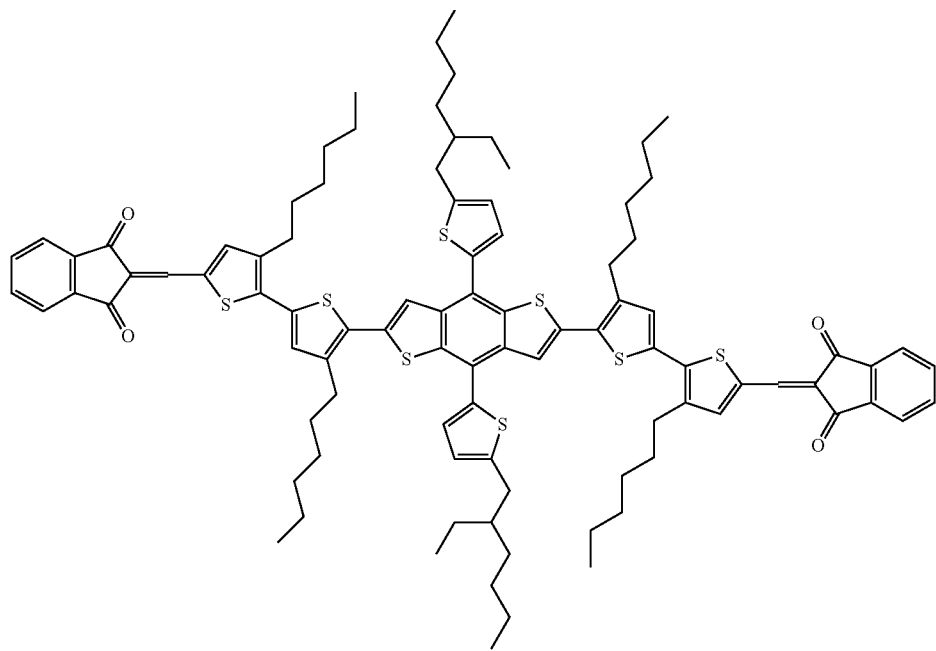
Exemplary Compound 2
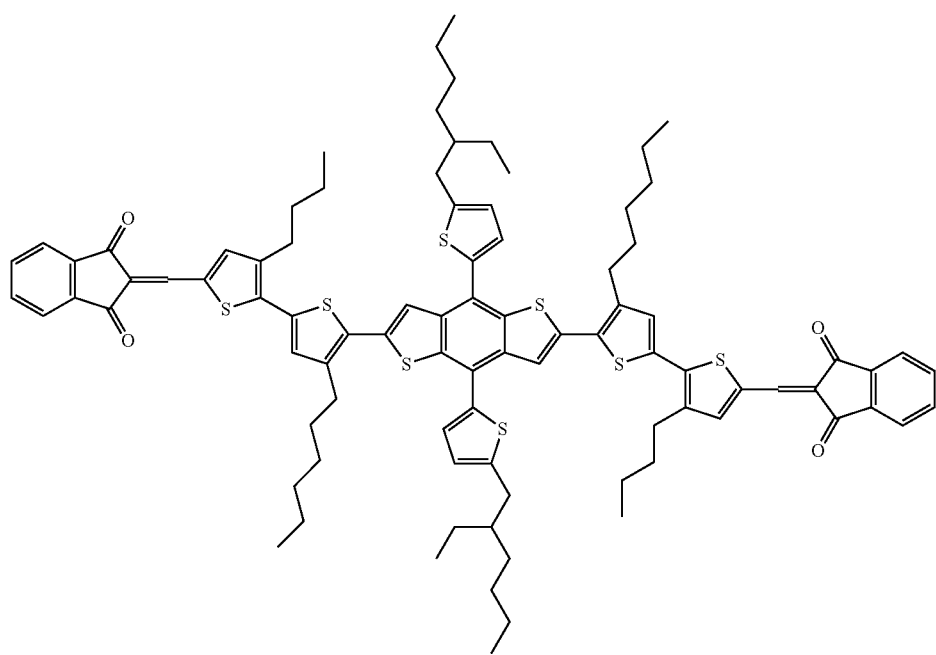

Exemplary Compound 3
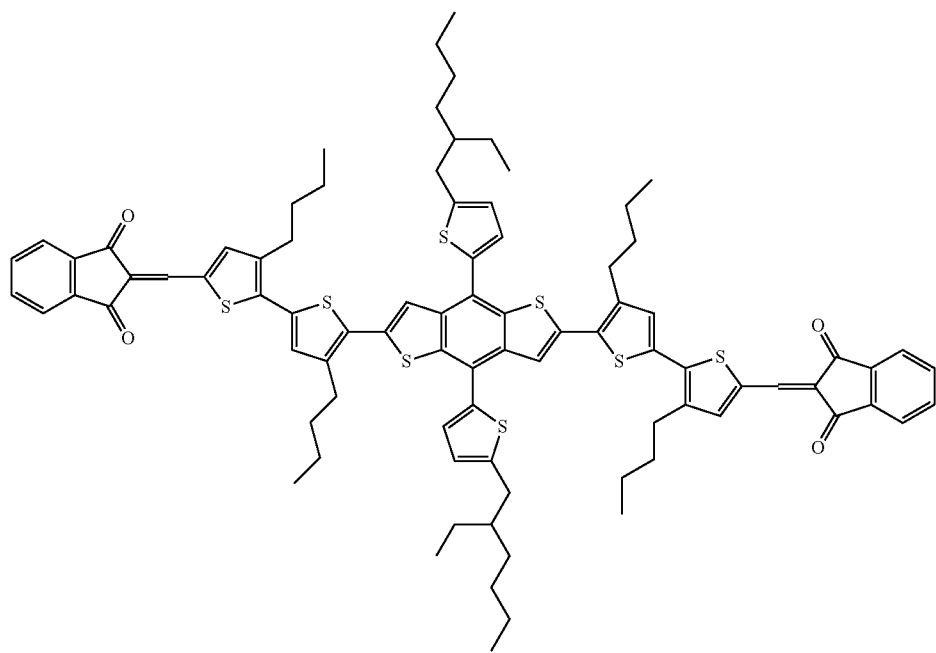
Exemplary Compound 4
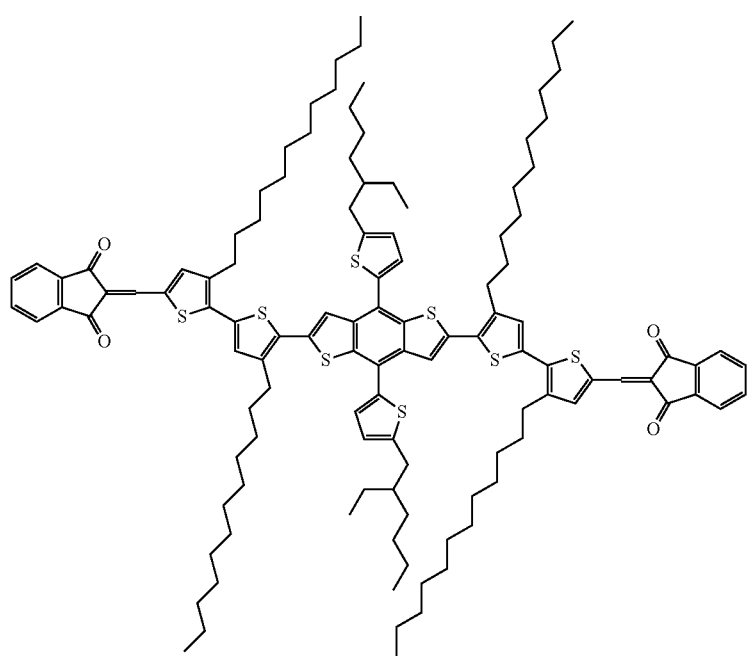

Exemplary Compound 5
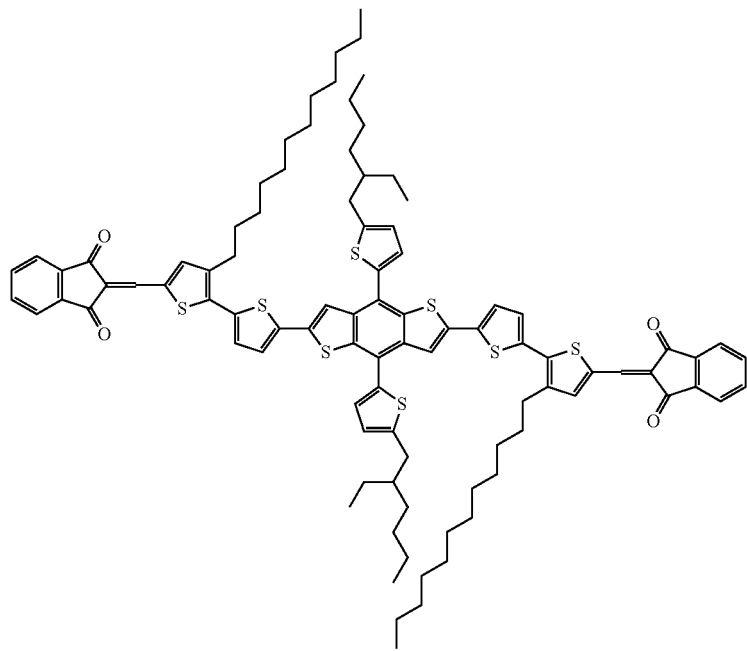
Exemplary Compound 6
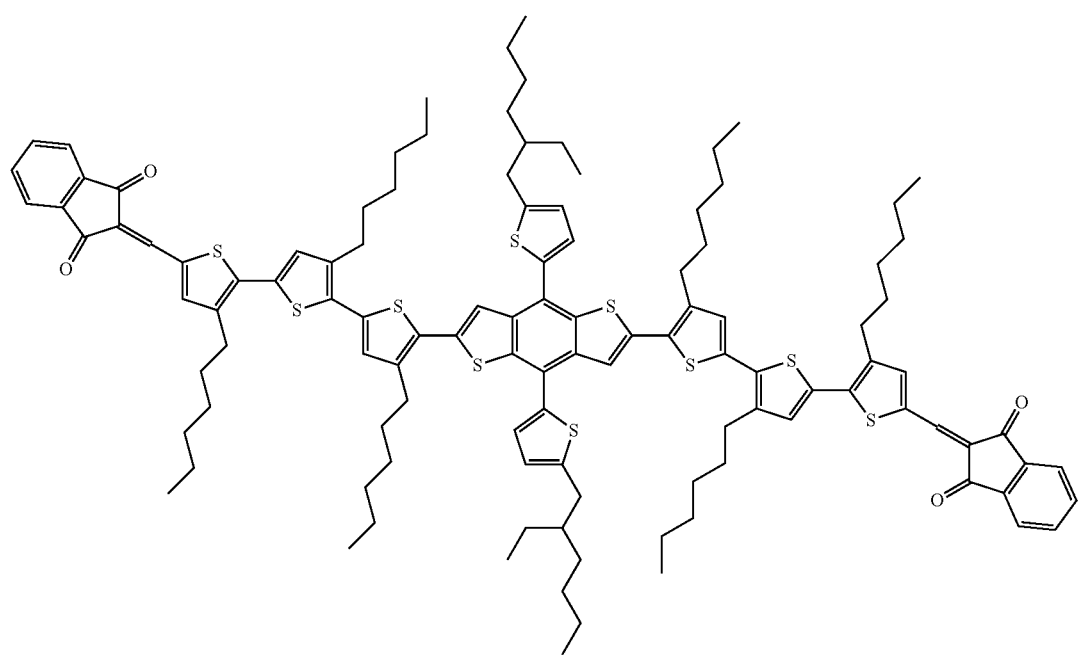

Exemplary Compound 7
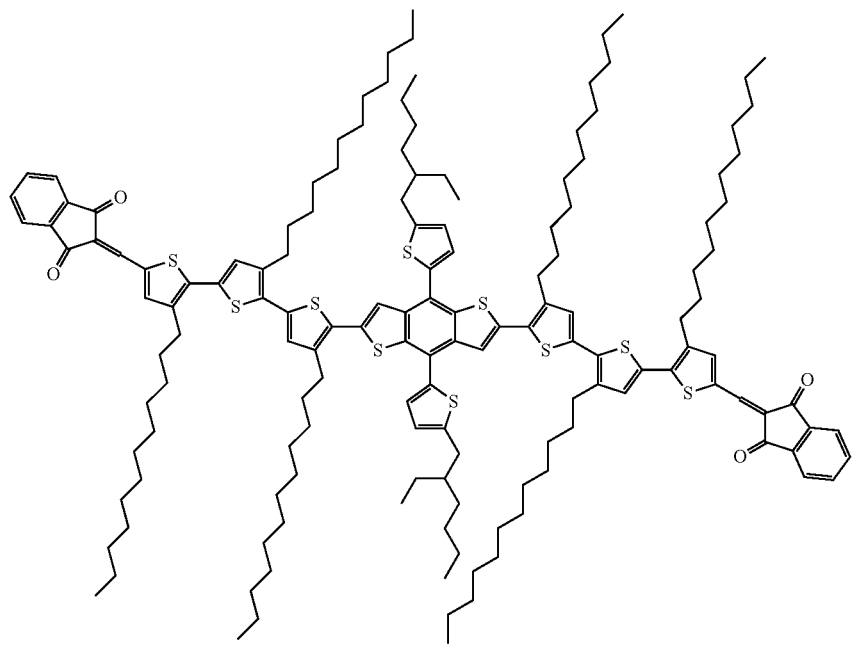
Exemplary Compound 8
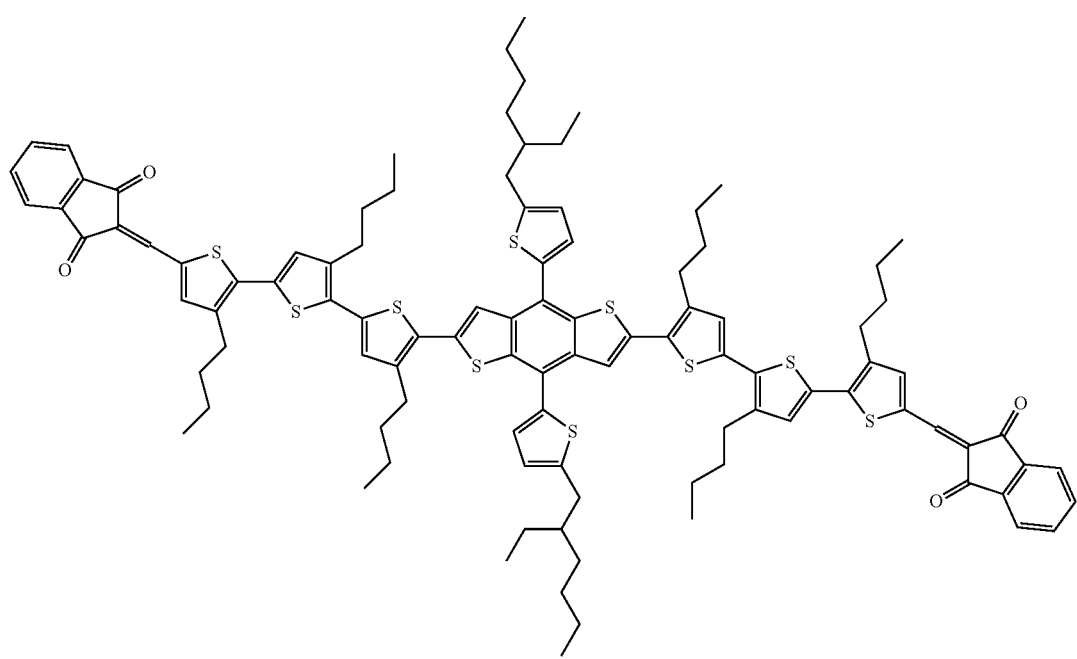

Exemplary Compound 9
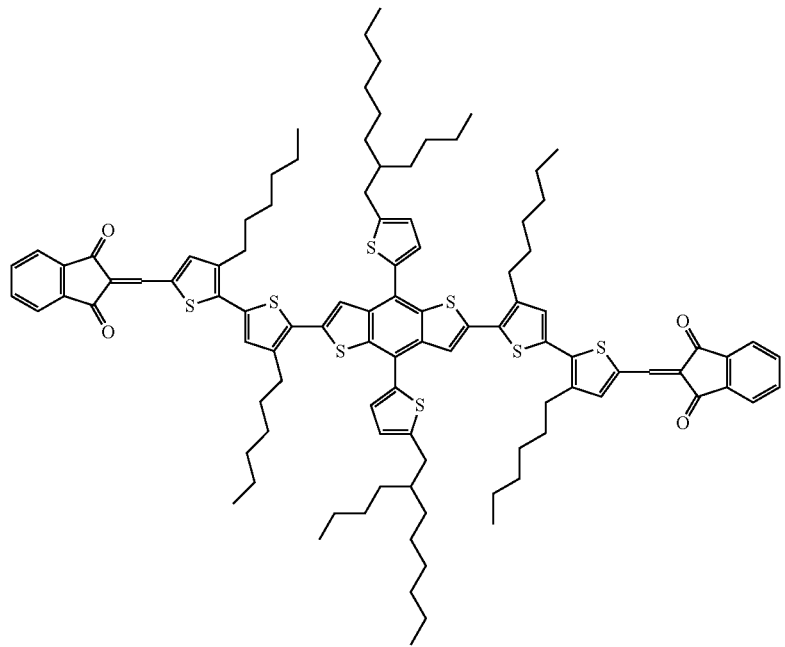
Exemplary Compound 10
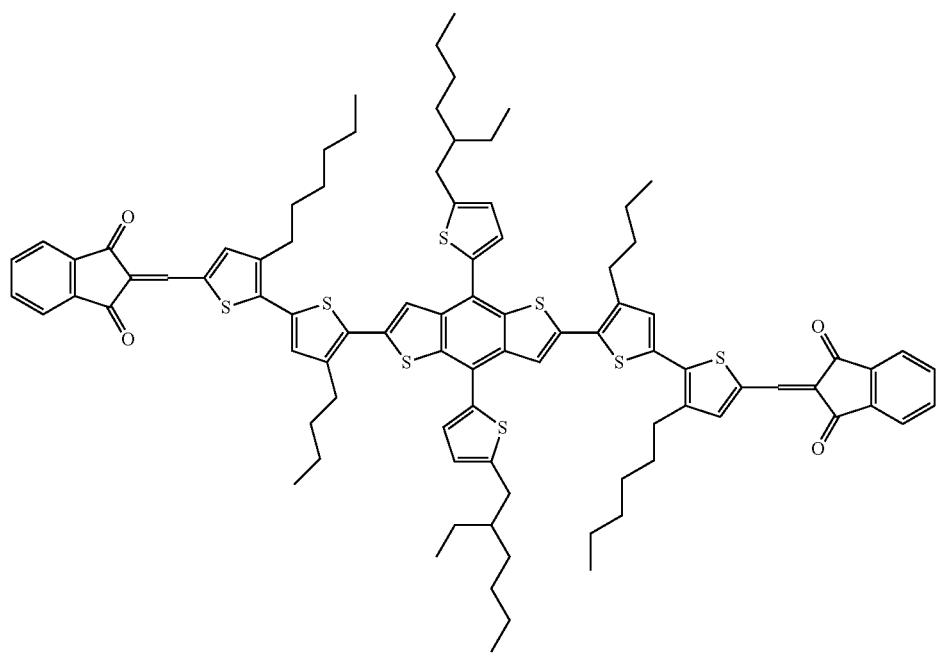

-continued
Exemplary Compound 11
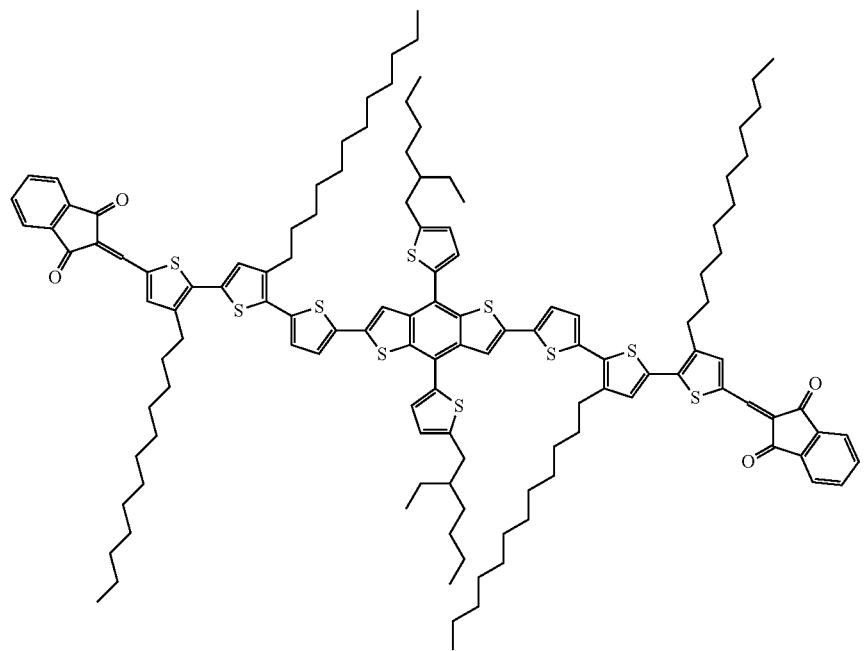
Exemplary Compound 12
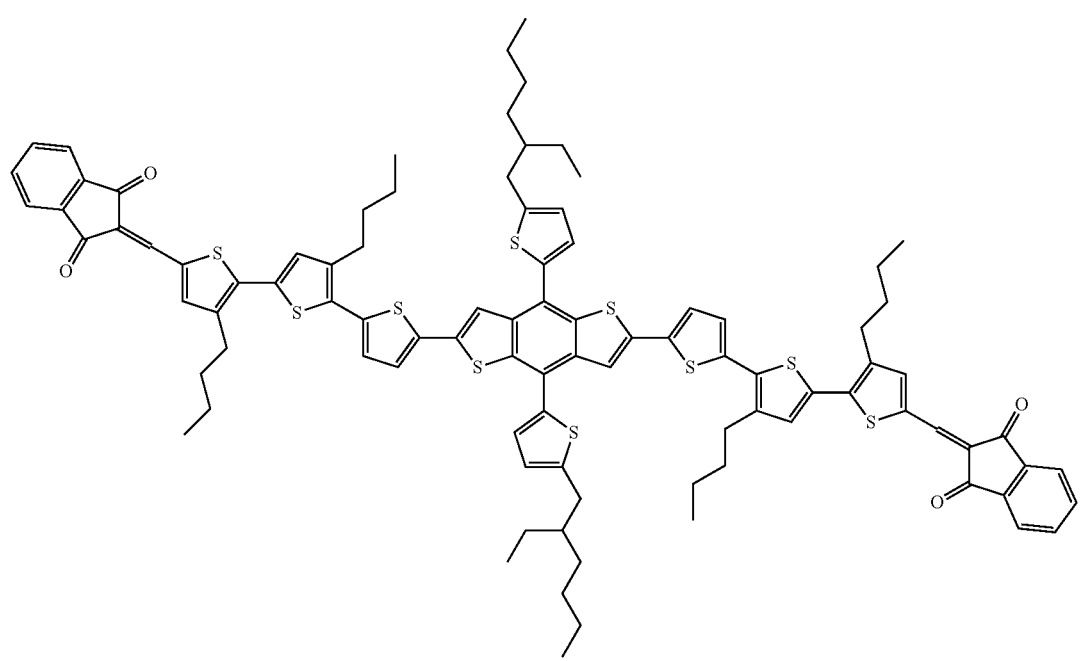

Exemplary Compound 13
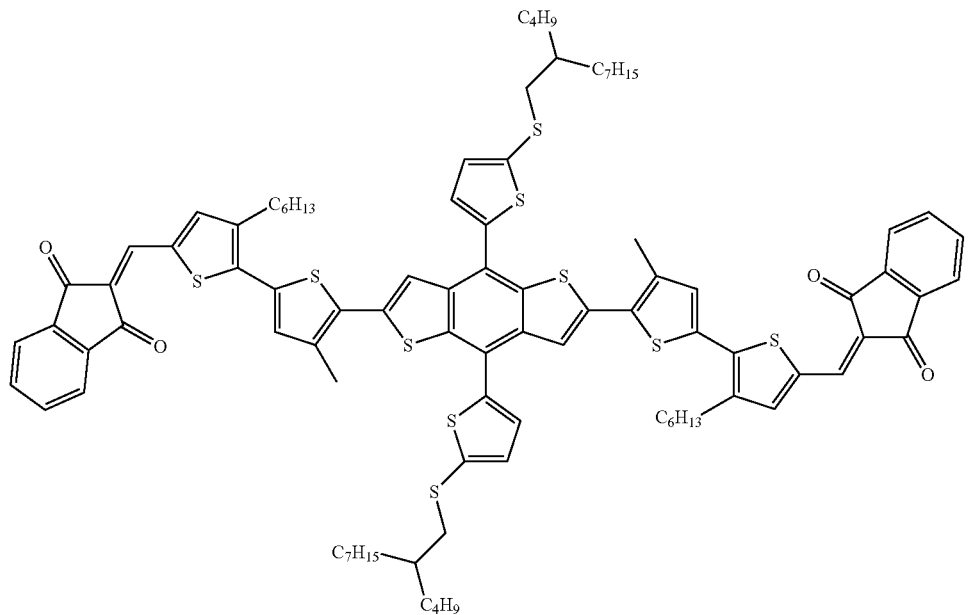
Exemplary Compound 14
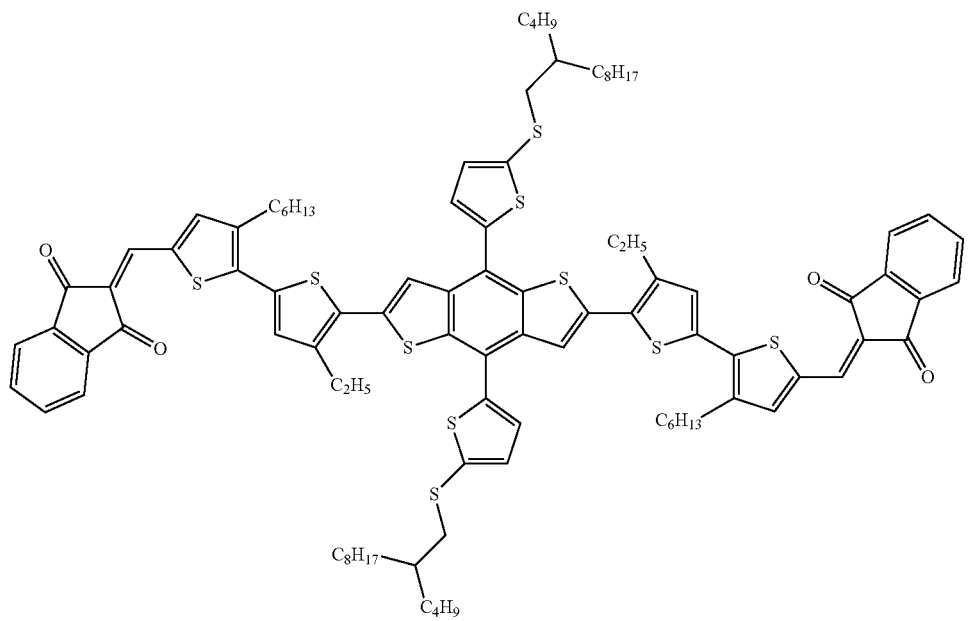

<Production Method of Organic Material Represented by General Formula (1)>
As a production method of the organic material represented by General Formula (1), for example, the organic material represented by General Formula (1) can be obtained by a first step through a fourth step.
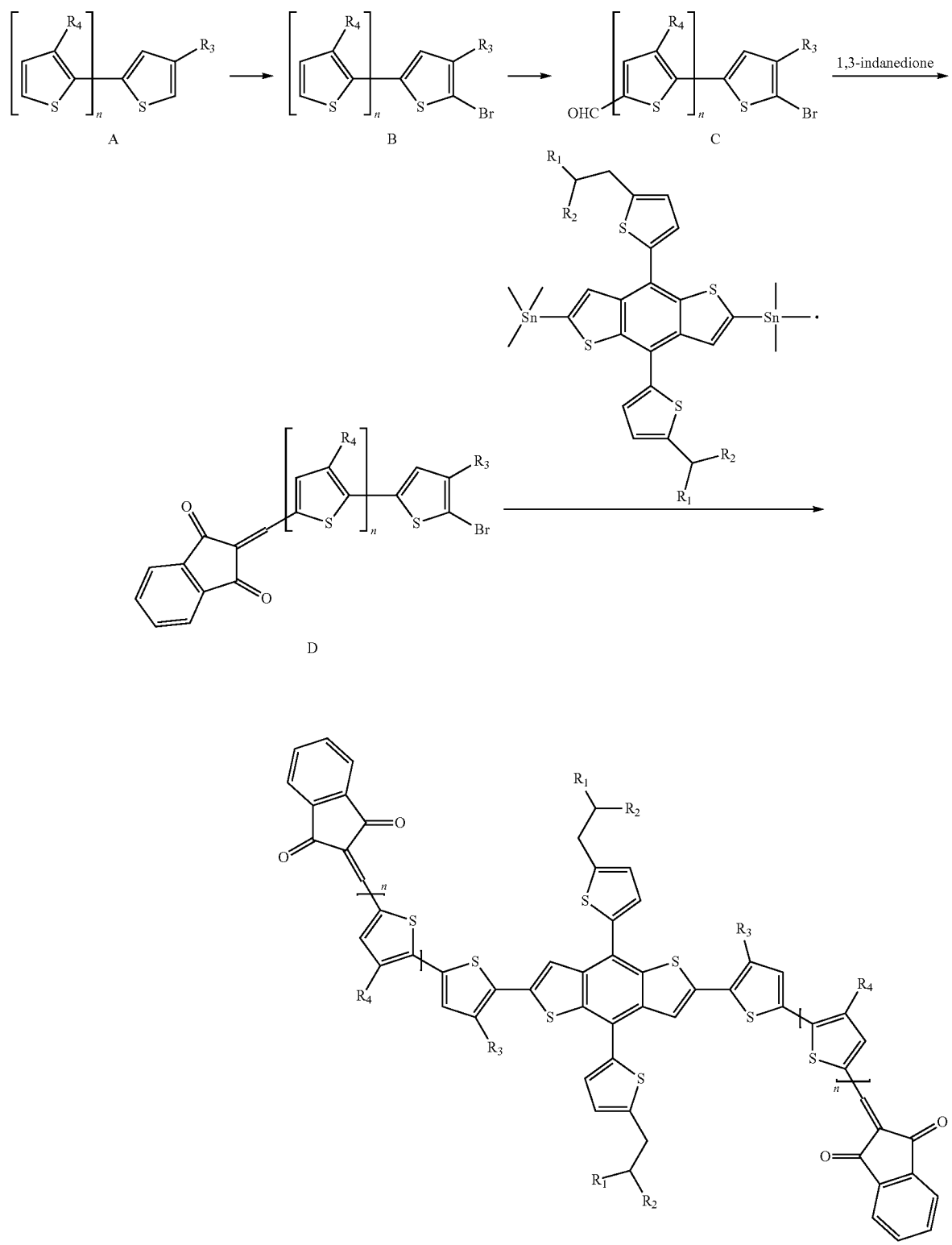

First Step

A brominating agent is allowed to act on Compound A to brominate the 2-position of bithiophene, to thereby obtain Compound B.

Second Step

The 5'-position of bithiophene of Compound B is formylated to obtain Compound C.

Third Step

Dehydration concentration is performed on Compound C to obtain Bithiophene Derivative D, in which 1,3-indandione is condensed.

Fourth Step

A tin product of a benzodithiophene derivative and Bithiophene Derivative D obtained in the third step are allowed to react through Stille coupling, to thereby obtain a target.

As the brominating agent in the first step, a typical brominating agent, such as N-bromosuccinimide and bromine, can be used. The solvent is not particularly limited, but a halogen-based solvent (e.g., chloroform, and dichloromethane) or an amide-based solvent (e.g., dimethylformamide) can be used. Moreover, an acid compound, such as acetic acid, may be used as the catalyst.

As the formylation in the second step, typical formulation including lithiation using alkyl lithium, such as n-butyllithium, followed by formulation using dimethylformamide, or formulation through the Vilsmeier reaction can be used. As the solvent, a solvent suitable for each reaction can be appropriately used.

In the third step, Bithiophene Derivative D can be obtained by dehydration condensation. The solvent for use is not particularly limited, as long as the solvent is suitable for the dehydration condensation.

In the fourth step, the target can be obtained through the Stille coupling reaction. As the catalyst, a palladium catalyst, such as tetrakis(triphenylphosfine)palladium, can be used. As the solvent, a typically used solvent, such as toluene and dimethylformamide, can be selected.

<<Photoelectric Conversion Element>>

The photoelectric conversion element of the present disclosure includes a substrate, and on the substrate, a first electrode, an electron-transporting layer, a photoelectric conversion layer, a hole-transporting layer, and a second electrode. The photoelectric conversion layer includes the organic material of the present disclosure and an n-type semiconductor material.

The photoelectric conversion element of the present disclosure is preferably a photoelectric conversion element, in which a first electrode, an electron-transporting layer, a photoelectric conversion layer, a hole-transporting layer, and a second electrode are sequentially disposed on a substrate, or a photoelectric conversion element, in which a first electrode, a hole-transporting layer, a photoelectric conversion layer, an electron-transporting layer, and a second electrode are sequentially disposed on a substrate. The photoelectric conversion layer preferably includes the organic material of the present disclosure and an n-type semiconductor material.

<Photoelectric Conversion Layer>

The photoelectric conversion layer includes at least the organic material of the present disclosure and an n-type semiconductor material, and may further include other components, if necessary.

(N-Type Semiconductor Material)

Examples of the n-type semiconductor material include fullerenes and fullerene derivatives. Among the above-listed examples, fullerene derivatives are preferable in view of charge separation and charge transport.

As the fullerene derivative, a fullerene derivative appropriately synthesized may be used, or a commercial product of the fullerene derivative may be used. Examples of the commercial product include PC71BM (phenyl C71 butyric acid methyl ester), PC61BM, indene fullerene bis adducts, and a fullerene derivative represented by General Formula (4) below.

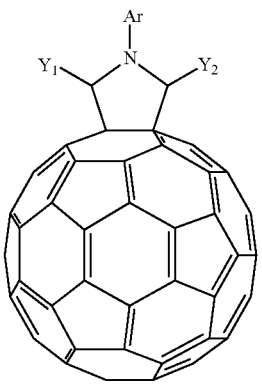

General Formula (4)

In General Formula (4), $Y_1$ and $Y_2$ are each independently a hydrogen atom, an alkyl group, an alkenyl group, an alkynyl group, an aryl group, or an aralkyl group with the proviso that both $Y_1$ and $Y_2$ are not hydrogen atoms at the same time, and Ar is an aryl group.

In General Formula (4), moreover, a site represented by:

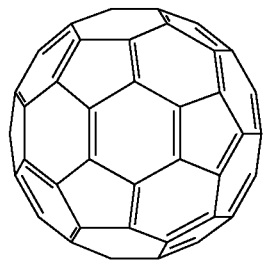

is a fullerene skeleton having 60 carbon atoms (C60 fullerene). The site represents the same in all of chemical formulae below.

The fullerene derivative represented by General Formula (4) is a compound that is easily formed into a thin film by coating, because the fullerene derivative has excellent solubility to various organic solvents. Moreover, the fullerene derivative is a compound with which high conversion efficiency is exhibited when the compound is used as an n-type semiconductor material to form a photoelectric conversion layer having a bulk heterojunction structure. Therefore, the fullerene derivative is a compound having excellent properties as an n-type semiconductor material for organic thin film solar cells.

Specific examples of the aryl group represented by Ar in General Formula (4) include a phenyl group, a naphthyl group, an anthranil group, and a phenanthryl group. The aryl group is particularly preferably a phenyl group.

The aryl group represented by Ar includes an aryl group having a substituent and an aryl group that does not have a substituent.

A substituent in the aryl group having a substituent represented by Ar is preferably free from an oxygen atom. Examples of the substituent include an aryl group, an alkyl group, a cyano group, an alkoxy group, and an alkoxycarbonyl group. Examples of the aryl group among the above-listed substituents include a phenyl group. Examples of the alkyl group and an alkyl group site of the alkoxy group include an alkyl group having from about 1 through about 20 carbon atoms, similarly to alkyl groups represented by $Y_1$ and $Y_2$ described below. The number of the substituents, and positions of substitution are not particularly limited. For example, about 1 through about 3 substituents may be present at arbitral positions of the aryl group represented by Ar.

Among groups represented by $Y_1$ and $Y_2$, the alkyl group is preferably an alkyl group having from about 1 through about 20 carbon atoms, more preferably an alkyl group having from about 1 through about 12 carbon atoms, and particularly preferably an alkyl group having from about 6 through about 12 carbon atoms. The above-listed alkyl groups may have a straight chain or a branched chain, but particularly preferably a straight chain. Note that, the alkyl group may further include 1 or 2 or more different elements, such as S and O, in a hydrocarbon chain.

Among groups represented by $Y_1$ and $Y_2$, the alkenyl group is preferably an alkenyl group having from about 2 through about 10 carbon atoms. Particularly preferable specific examples of the alkenyl group include a straight-chain or branched-chain alkenyl group having from 2 through 4 carbon atoms, such as a vinyl group, a 1-propenyl group, an allyl group, an isopropenyl group, a 1-butenyl group, a 2-butenyl group, a 3-butenyl group, a 1-methyl-2-propenyl group, and a 1,3-butadienyl group.

Among groups represented by $Y_1$ and $Y_2$, the alkynyl group is preferably an alkynyl group having from about 1 through about 10 carbon atoms. Particularly preferable specific examples of the alkenyl group include a straight-chain or branched-chain alkynyl group having from 2 through 4 carbon atoms, such as an ethynyl group, a 1-propynyl group, a 2-propynyl group, a 1-methyl-2-propynyl group, a 1-butynyl group, a 2-butynyl group, and a 3-butynyl group.

Examples of the aryl group among groups represented by $Y_1$ and $Y_2$ include a phenyl group, a naphthyl group, an anthranil group, and a phenanthryl group.

Examples of the aralkyl group among groups represented by $Y_1$ and $Y_2$ include an aralkyl group having from about 7 through about 20 carbon atoms, such as 2-phenylethyl, benzyl, 1-phenylethyl, 3-phenylpropyl, and 4-phenylbutyl.

The alkyl group, the alkenyl group, the alkynyl group, the aryl group, the aralkyl group that are groups represented by $Y_1$ and $Y_2$ may have a substituent, or may not have a substituent.

Examples of the substituent, which the groups represented by $Y_1$ and $Y_2$ may have, include an alkyl group, an alkoxycarbonyl group, a polyether group, an alkanoyl group, an amino group, an aminocarbonyl group, an alkoxy group, an alkylthio group, a group: —CONHCOR' (in the formula, R' is an alkyl group), a group: —C(=NR')—R'' (in the formula, R' and R'' are each an alkyl group), and a group: —NR'=CR''R''' (in the formula, R', R'', and R''' are each an alkyl group).

Examples of the polyether group among the above-listed substituents include a group represented by a formula: $Y_3$—$(OY_4)n$-O—. In the formula, $Y_3$ is a monovalent hydrocarbon group, such as an alkyl group, and $Y_4$ is a bivalent aliphatic hydrocarbon group. Specific examples of the repeating unit represented by —$(OY_4)n$- in the polyether group represented by the formula above include alkoxy chains, such as —$(OCH_2)n$-, —$(OC_2H_4)n$-, and —$(OC_3H_6)n$-. The repeating number n of any of the above-listed repeating units is preferably from about 1 through about 20, and more preferably from about 1 through about 5. The repeating unit represented by —$(OY_4)n$- may not include only an identical repeating unit, but also may include two or more different repeating units. Among the above-listed repeating units, each of —$OC_2H_4$— and —$OC_3H_6$— may be a straight chain or a branched chain.

Among the above-listed substituents, moreover, the alkyl group, and an alkyl group site in the alkoxycarbonyl group, the alkanoyl group, the alkoxy group, the alkylthio group, the polyether group, the group:
CONHCOR', the group: —C(=NR')—R'', and the group: —NR'=CR''R''' are each preferably an alkyl group having from about 1 through about 20 carbon atoms, more preferably an alkyl group having from about 1 through about 12 carbon atoms, and particularly preferably an alkyl group having from about 6 through about 12 carbon atoms, similarly to the above-mentioned alkyl group.

The amino group, and an amino group site in the aminocarbonyl group are each particularly preferably an amino group bonded to one or two alkyl groups each having from about 1 through about 20 carbon atoms.

Among the fullerene derivatives represented by General Formula (4), examples of the compound having preferable properties include compounds where Ar is a phenyl group that may have a substituent or may not have a substituent, one of $Y_1$ and $Y_2$ is a hydrogen atom, and the other is an alkyl group having an alkoxycarbonyl group as a substituent, an alkyl group having an alkoxy group as a substituent, an alkyl group having a polyether group as a substituent, an alkyl group having an amino group as a substituent, or a phenyl group that may have a substituent or may not have a substituent.

Among the compounds, examples of the compound having particularly preferable properties include compounds where Ar is a phenyl group that may have a phenyl group, a cyano group, an alkoxy group, an alkoxycarbonyl group, or an alkyl group as a substituent, or may not have a substituent, one of $Y_1$ and $Y_2$ is a hydrogen atom, and the other is an alkyl group having an alkoxycarbonyl group as a substituent, an alkyl group having an alkoxy group as a substituent, an alkyl group having a polyether group as a substituent, a phenyl group, a phenyl group having an alkyl group as a substituent, a phenyl group having an alkoxycarbonyl group as a substituent, or a phenyl group having an alkoxy group as a substituent. The above-listed compounds are compounds including groups having appropriate polarity on a pyrrolidine skeleton, and have excellent self-organization properties. Therefore, it is assumed that each of the compounds can form a photoconversion site of a bulk heterojunction structure having an appropriate layer separation structure when a photoconverison layer of a bulk heterojunction structure is formed, and as a result, electron mobility is improved to exhibit high conversion efficiency. The more preferable compound is a compound where Ar is a phenyl group, one of $Y_1$ and $Y_2$ is a hydrogen atom, and the other is an unsubstituted alkyl group (alkyl group having from 4 through 6 carbon atoms), an unsubstituted phenyl group, a 1-naphthyl group, or 2-naphthyl group, or a compound represented by General Formula (5).

General Formula (5)

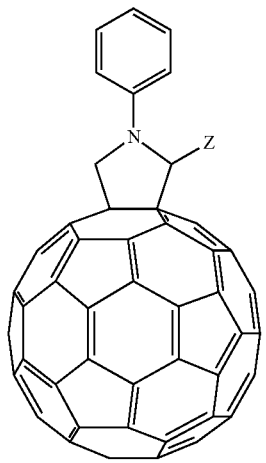

In General Formula (5), Z is a phenyl group, a 1-naphthyl group, or a 2-naphthyl group.

Examples of the phenyl group that is a group represented by Z include a phenyl group having a substituent, and a phenyl group that does not have a substituent. Examples of the 1-naphthyl group that is a group represented by Z include a 1-naphthyl group having a substituent, and 1-naphthyl group that does not have a substituent. Examples of the 2-naphthyl group that is a group represented by Z include a 2-naphthyl group having a substituent, and a 2-naphthyl group that does not have a substituent.

Note that, the photoelectric conversion layer may include, as well as the n-type semiconductor material, an inorganic compound, such as zinc oxide, and titanium oxide.

An amount of the n-type semiconductor material relative to a total amount of a solution for the photoelectric conversion layer is preferably from 0.2% by mass through 10% by mass.

The above-mentioned other components are not particularly limited and may be appropriately selected depending on the intended purpose. Examples of the above-mentioned other components include various additives, such as diiodooctane, octanedithiol, and chloro naphthalene.

An average thickness of the photoelectric conversion layer is preferably from 50 nm through 400 nm, and more preferably from 60 nm through 250 nm. When the average thickness is less than 50 nm, an amount of light absorbed by the photoelectric conversion layer is small, and generation of carriers may be insufficient. When the average thickness is greater than 400 nm, transport efficiency of carriers generated by light absorption may be further decreased.

In the present disclosure, the organic material and the n-type semiconductor material may be sequentially formed to form a flat junction interface. In order to increase a junction interface, however, a bulk heterojunction where the above-mentioned materials are three-dimensionally mixed is preferably formed.

In case of materials having high solubility, the organic material and the n-type semiconductor material are dissolved in a solvent to form a solution where the organic material and the n-type semiconductor material are mixed in the state of molecules, the solution is applied and dried, and then the solvent is removed to form the bulk heterojunction. Moreover, a heating treatment may be performed to optimize an aggregation state of each semiconductor.

Note that, in case where materials having poor solubility are used, a mix layer can be also formed by preparing a solution in which an n-type semiconductor material is dispersed in a solvent, in which the organic material of the present disclosure is dissolved, and applying the solution. In this case, a heating treatment may be further performed to optimize an aggregation state of each semiconductor.

The organic material used in the present disclosure has excellent heat resistance because the organic material can easily form an aggregate structure, and is rigid. Moreover, the organic material has a deep HOMO level and air stability of the organic material is excellent, as well as that an improvement of open-circuit voltage owing to the material is expected. In addition, an organic semiconductor film having a regular coagulate state, such as crystallinity, and orientation, can be more effectively formed by introducing a soluble group, such as an alkyl group, into the above-mentioned rigid molecular skeleton, while maintaining solubility to typical organic solvents. In the above-mentioned state of high regularity, high charge transport can be expected. Particularly, in General Formula (1), an alkyl group of a thiophene group substituting benzodithiophene is a branched-chain alkyl group. Since the alkyl group is a branched chain, solubility is significantly enhanced. As a result, an organic thin film can be made thick. Since the organic thin film is thick, a large amount of light can be absorbed, leading to an improvement of power generation.

Meanwhile, in the organic material disclosed in "Chem. Mater. 2013, 25, 2274-2281," an alkyl group of a thiophene group substituting benzodithiophene is a straight chain. In this case, although it is also clearly described in Examples, the organic material has low solubility, and it is difficult to form a thick organic thin film. The organic material represented by General Formula (1) having a branched alkyl chain has higher solubility, and is more advantageous for forming a thick film.

In the case where a photoelectric conversion layer is formed by mixing the organic material represented by General Formula (1) and the n-type semiconductor material, the organic material represented by General Formula (1) and the n-type semiconductor material are added to a solvent at the predetermined mass ratio, the organic material and the n-type semiconductor material are dissolved by a method, such as heating, stirring, ultrasonic wave radiation, to form a solution, and the solution is applied onto an electrode. In the formation of the photoelectric conversion layer, use of two or more solvents in mixture can improve photoelectric conversion efficiency of a photoelectric conversion element.

A concentration of total solids in a solution for forming the photoelectric conversion layer is preferably from 1% by mass through 10% by mass. Moreover, a ratio between the organic material represented by General Formula (1) and the n-type semiconductor material based on a mass ratio is preferably from 40:60 through 80:20.

The solvent is not particularly limited and may be appropriately selected depending on the intended purpose. Examples of the solvent include methanol, ethanol, butanol, toluene, xylene, o-chlorophenol, acetone, ethyl acetate, ethylene glycol, tetrahydrofuran, dichloromethane, chloroform, dichloroethane, chlorobenzene, dichlorobenzene, trichlorobenzene, chloronaphthalene, dimethylformamide, dimethylsulfoxide, N-methylpyrrolidone, and γ-butyrolactone. The above-listed examples may be used alone or in combination. Among the above-listed examples, chlorobenzene, chloroform, and ortho-dichlorobenzene are preferable.

Examples of a formation method of a thin film of an organic material to be the photoelectric conversion layer include spin coating, blade coating, slit-die coating, screen-printing coating, bar-coater coating, mold coating, print transfer, dip coating, inkjet printing, spray coating, and vacuum vapor deposition. Among the above-listed examples, the formation method can be appropriately selected depending on properties of a thin organic material film to be produced, such as thickness controlling, and orientation controlling.

In the case where spin coating is performed, for example, a concentration of the organic material having a structure represented by General Formula (1) and the n-type semiconductor material is preferably from 5 mg/mL through 40 mg/mL (a mass of the organic material having a structure represented by General Formula (1) and the n-type semiconductor material relative to a volume of a solution including the organic material having a structure represented by General Formula (1), the n-type semiconductor material, and a solvent). At the above-mentioned concentration, a uniform photoelectric conversion layer can be easily formed.

In order to remove the organic solvent, an annealing treatment may be performed on the produced photoelectric conversion layer under reduced pressure or an inert atmosphere (a nitrogen or argon atmosphere). A temperature of the annealing treatment is preferably from 40° C. through 300° C., and more preferably from 50° C. through 150° C. Since the annealing treatment is performed, moreover, stacked layers are penetrated into each other at interfaces, to thereby increase a contact effective area. As a result, a short-circuit current may be increased. Note that, the annealing treatment may be performed after forming electrodes.

The photoelectric conversion element of the present disclosure is described with reference to drawings.

Figure 2:
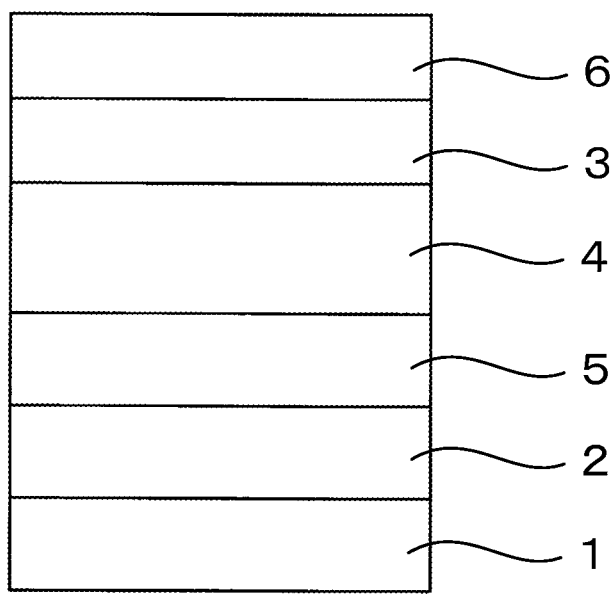
FIG. 2 is a schematic view illustrating another example of a structure of the photoelectric conversion element of the present disclosure.

FIG. 1 illustrates a structure where a first electrode 2, an electron-transporting layer 3, a photoelectric conversion layer 4, a hole-transporting layer 5, and a second electrode 6 are sequentially disposed on a substrate 1. FIG. 2 illustrates a structure where a first electrode 2, a hole-transporting layer 5, a photoelectric conversion layer 4, an electron-transporting layer 3, and a second electrode 6 are sequentially disposed on a substrate 1.

<Substrate>

A substrate for use in the present disclosure is not particularly limited and any of substrates known in the art can be used. The substrate 1 is preferably formed of a transparent material. Examples of the transparent material include glass, transparent plastic plates, transparent plastic films, and transparent inorganic crystals.

<Electrodes>

At least one of the first electrode and the second electrode is an electrode transparent to visible light, and the other electrode may be transparent or not transparent to visible light.

The electrode transparent to visible light is not particularly limited, and known electrodes used for typical photoelectric conversion elements or liquid crystal panels can be used. Examples of the electrode transparent to visible light include conductive metal oxides, such as tin-doped indium oxide (referred to as "ITO" hereinafter), fluorine-doped tin oxide (referred to as "FTO" hereinafter), antimony-doped tin oxide (referred to as "ATO" hereinafter), and aluminium- or gallium-doped zinc oxide (referred respectively as "AZO," and "GZO" hereinafter).

An average thickness of the electrode transparent to visible light is preferably from 5 nm through 10 μm, and more preferably from 50 nm through 1 μm.

In order to maintain certain hardness, the electrode transparent to visible light is preferably disposed on a substrate composed of a material transparent to visible light. A product of the electrode and the substrate that are integrated can also be used. Examples of the integrated product include FTO coated glass, ITO coated glass, zinc oxide-aluminium coated glass, FTO coated transparent plastic films, and ITO coated transparent plastic films.

The electrode transparent to visible light may be an electrode containing a substrate (e.g., a glass substrate) on which a metal electrode having the structure through which light can pass (e.g., a mesh-patterned structure or a stripe-patterned structure) is disposed. Alternatively, the electrode transparent to visible light may be an electrode where carbon nanotube or graphene is laminated on the substrate in a manner that transparency is secured. These may be used alone, or in combination, or in the state of a laminate.

In order to reduce substrate resistance, moreover, a metal lead wire may be used. Examples of a material of the metal lead wire include metals, such as aluminium, copper, silver, gold, platinum, and nickel.

The metal lead wire is disposed on the substrate, for example, by vapor deposition, sputtering, or crimping, followed by disposing ITO or FTO on the metal.

Examples of the electrode that is not transparent to visible light, which is used as at least one of the first electrode and the second electrode, include metals (e.g., platinum, gold, silver, copper, and Al) and graphite. A thickness of the electrode that is not transparent to visible light is not particularly limited, and the electrode that is not transparent to visible light may be composed of a single layer, or a laminate including two or more layers.

<Electron-Transporting Layer>

The electron-transporting layer is not particularly limited and any of electron-transporting layers known in the art can be used. The electron-transporting layer is preferably formed of a first layer including metal oxide and a second layer disposed between the first layer and the photoelectric conversion layer, where the second layer includes an amine compound represented by General Formula (6) below. Properties can be improved by disposing the second layer.

<Electron-Transporting Layer (First Layer)>

A material for forming the electron-transporting layer may be appropriately selected depending on the intended purpose. For example, the electron-transporting layer is formed by applying an electron-accepting organic material [e.g., perylenetetracarboxylic anhydride, perylenetetracarboxylic diimide, oxazole derivatives, triazol derivatives, phenanthroline derivatives, phosphine oxide derivatives, fullerene compounds, CNT, and CN-PPV], or an inorganic material (e.g., zinc oxide, titanium oxide, lithium fluoride, and calcium metal) through a sol-gel method or sputtering. Among the above-listed examples, metal oxides, such as zinc oxide, titanium oxide, and tin oxide, are preferable.

An average thickness of the electron-transporting layer is not particularly limited and may be appropriately selected depending on the intended purpose. The electron-transporting layer preferably covers the entire surface as thin as possible, and more preferably has an average thickness of from 10 nm through 100 nm.

<Electron-Transporting Layer (Second Layer)>

The second layer formed on the first layer of the electron-transporting layer preferably includes an amine compound represented by General Formula (6) below.

General Formula (6)

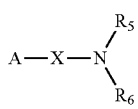

$R_5$ and $R_6$ are each independently an alkyl group having from 1 through 4 carbon atoms, where $R_5$ and $R_6$ may be bonded to each other to form a ring.

The alkyl group includes an alkyl group including a substituent and an alkyl group including no substituent. Specific examples of the alkyl group include a methyl group, an ethyl group, and a benzyl group. The alkyl group is preferably a methyl group.

X is a bivalent aromatic group having from 6 through 14 carbon atoms or an alkylene group from 1 through 4 carbon atoms. Specific examples of X include a bivalent benzene group, a bivalent naphthalene group, and a bivalent anthracene group. X is preferably a bivalent benzene group. A is any of substituents below.

—COOH

—P(=O)(OH)$_2$

—Si(OH)$_3$

A is preferably —COOH.

An average thickness of the second layer is not particularly limited and may be appropriately selected depending on the intended purpose. The second layer preferably covers the entire surface as thin as possible, and an average thickness of the second layer is preferably from 0.1 nm through 10 nm.

<Hole-Transporting Layer>

The hole-transporting layer is disposed to improve a collection efficiency of holes. Specifically, the hole-transporting layer is formed by depositing a hole-transporting organic compound, such as a conductive polymer [e.g., PEDOT:PSS (polyethylene dioxythiophene:polystyrene sulfonic acid)] and an aromatic amine derivative, or an inorganic compound having hole-transporting properties, such as molybdenum oxide, vanadium oxide, and nickel oxide, through spin coating, a sol-gel method, or sputtering. In the present disclosure, molybdenum oxide is preferably disposed.

An average thickness of the hole-transporting layer is not particularly limited, and may be appropriately selected depending on the intended purpose. The hole-transporting layer preferably covers the entire surface as thin as possible, and the average thickness of the hole-transporting layer is more preferably from 1 nm through 50 nm.

<Other Members>

The photoelectric conversion element of the present disclosure include other members, in addition to the substrate, the first electrode, the electron-transporting layer, the photoelectric conversion layer, the hole-transporting layer, and the second electrode. The above-mentioned other members are not particularly limited, and may be appropriately selected depending on the intended purpose. Examples of the above-mentioned other members include a gas barrier layer, a protective layer, and a buffer layer.

Examples of a material of the gas barrier layer include inorganic materials, such as, silicon nitride and silicon oxide.

The photoelectric conversion element of the present disclosure may have a series junction formed by stacking two or more photoelectric conversion layers (making as a tandem) via one or more intermediate electrodes.

Examples of the laminate structure include a laminate structure including a substrate, a first electrode, a hole-transporting layer, a first photoelectric conversion layer, an intermediate electrode, a second photoelectric conversion layer, an electron-transporting layer, and a second electrode in this order. Use of the laminate can improve open-circuit voltage.

In case of the above-described laminate structure, at least one of the photoelectric conversion layers includes an organic material thin film formed of the organic material represented by General Formula (1), and the other photoelectric conversion layer include another organic material having an absorption wavelength different from that of the organic compound represented by General Formula (1), in order to prevent reduction of short-circuit current.

Examples of the another organic material include: polymer materials, such as polythiophene compounds, polyphenylene vinylene compounds, polyfluorene compounds, and polyphenylene compounds; and low-molecular-weight materials, such as various porphyrins, and phthalocyanine.

<Use>

Recently, there is a need for, especially as an energy harvesting element, a photoelectric conversion element capable of efficiently generating electric power with weak light. Typical examples of weak light include LED light, and light of a fluorescent lamp. The above-mentioned light is typically used indoor, and is called indoor light. The illuminance of the indoor light is from about 20 Lux through about 1,000 Lux, and the indoor light is very weak light compared to direct sunlight (about 100,000 Lux).

The photoelectric conversion element of the present disclosure exhibits high conversion efficiency with weak light, such as the above-mentioned indoor light, and can be applied for a power supply by using in combination with a circuit board capable of controlling the generated electric current. Examples of a device utilizing the power supply include calculators, and watches. Other than the above-listed examples, a power supply containing the photoelectric conversion element of the present disclosure can be used in mobile phones, electric organizers, and electronic paper. Moreover, a power supply containing the photoelectric conversion element of the present disclosure can also be used as an auxiliary power for extending continuous usage of rechargeable or battery-driven electric appliances. Furthermore, the photoelectric conversion element of the present disclosure can be also applied as an image sensor.

EXAMPLES

The present disclosure will be described in more detail by way of the following Examples. However, the present disclosure should not be construed as being limited to these Examples.

Example I-1

Exemplary Compound 1 was synthesized according to the following scheme.

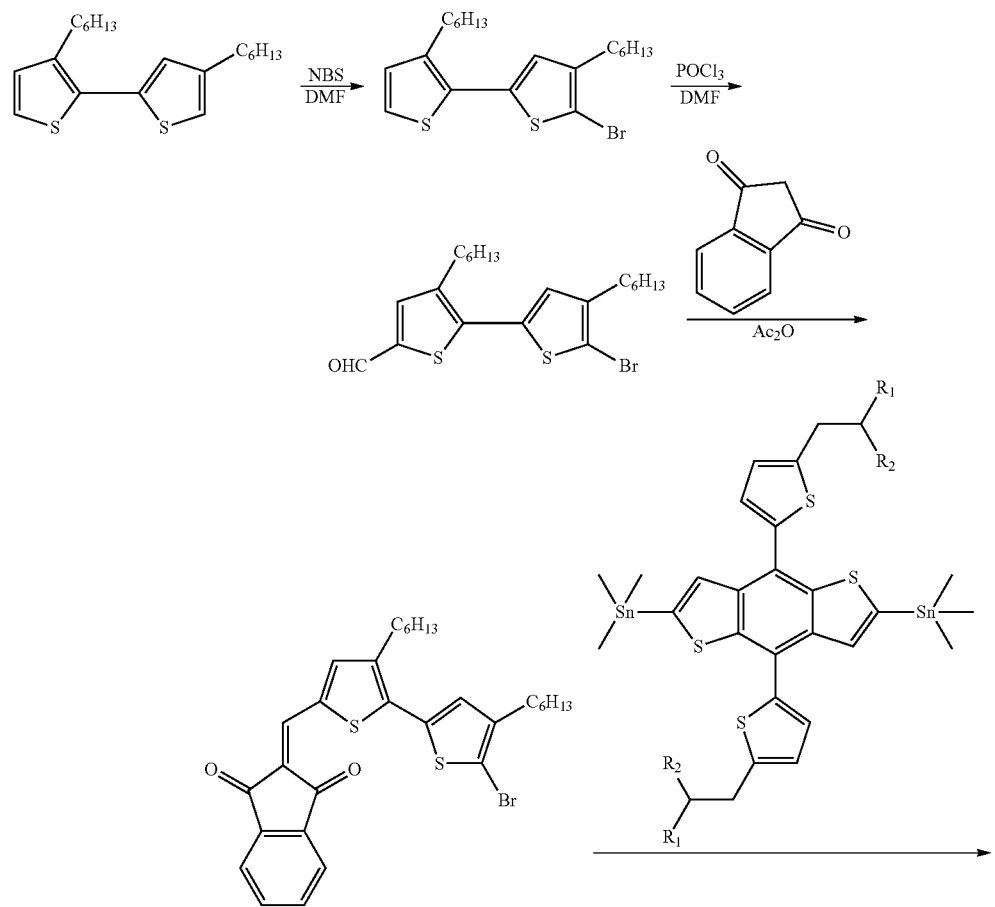
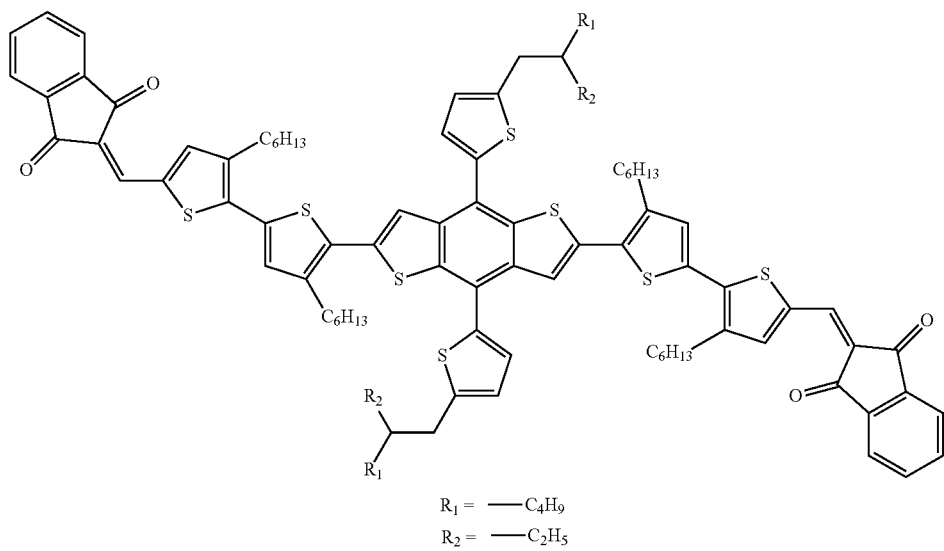
$R_1 = \text{—} C_4H_9$
$R_2 = \text{—} C_2H_5$
Exemplary Compound 1

(1-1) Synthesis of 5'-bromo-3,4'-dihexyl-2,2'-bithiophene

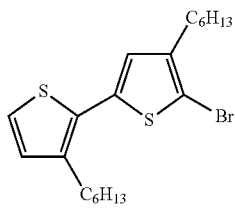

A Schlenk flask was charged with 3,4'-dihexyl-2,2'-bithiophene (5.0 g, 15 mmol) and dehydrated DMF (50 mL), and the mixture was stirred in a nitrogen atmosphere at 5° C. After slowly adding NBS (2.7 g, 15 mmol) to the mixture, the resultant mixture was stirred for 2 hours. Water was poured into the resultant reaction solution to perform extraction with hexane, followed by drying with sodium sulfate. The solvent was removed from the resultant by an evaporator. The resultant was separated by column chromatography (silica gel, hexane), to thereby obtain yellow oil (5.9 g, yield: 95%).

$^1$H NMR (400 MHz, CDCl$_3$): δ7.16 (d, J=5.2 Hz, 1H), 6.91 (d, J=5.2 Hz, 1H), 6.78 (s, 1H), 2.70 (t, J=7.6 Hz, 2H), 2.55 (t, J=7.6 Hz, 2H), 1.67-1.55 (m, 4H), 1.39-1.25 (m, 12H), 0.92-0.85 (m, 6H) (1-2) Synthesis of 5'-bromo-3,4'-dihexyl-[2,2'-bithiophene]-5-carbaldehyde

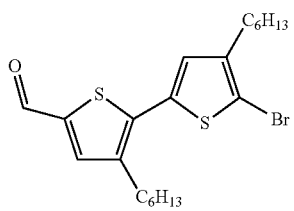

A Schlenk flask was charged with 5'-bromo-3,4'-dihexyl-2,2'-bithiophene (3.3 g, 8.0 mmol) and dehydrated DMF (25 mL), and the mixture was stirred in a nitrogen atmosphere at 0° C. After adding POCl$_3$ (1.8 g, 12 mmol) to the mixture, the resultant mixture was stirred for 24 hours at 80° C. Water was poured into the resultant reaction solution to perform extraction with hexane, followed by drying with sodium sulfate. The solvent was removed from the resultant by an evaporator. The resultant was separated by column chromatography (silica gel, chloroform:hexane=1:1), to thereby obtain dark yellow oil (2.0 g, yield; 57%).

$^1$H NMR (400 MHz, CDCl$_3$): δ9.82 (s, 1H), 7.57 (s, 1H), 6.96 (s, 1H), 2.74 (t, J=7.6 Hz, 2H), 2.57 (t, J=7.6 Hz, 2H), 1.70-1.57 (m, 4H), 1.44-1.23 (m, 12H), 0.96-0.83 (m, 6H)

(1-3) Synthesis of 2-((5'-bromo-3,4'-dihexyl-[2,2'-bithiophen]-5-yl)methylene)-1H-indene-1,3(2H)-dione

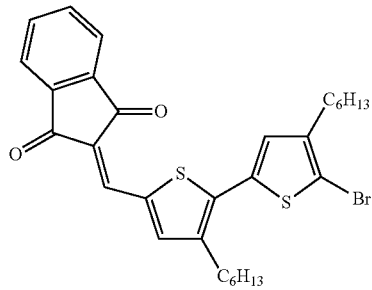

A Schlenk flask was charged with 5'-bromo-3,4'-dihexyl-[2,2'-bithiophene]-5-carbaldehyde (1.6 g, 3.6 mmol), 1H-indene-1,3(2H)-dione (0.82 g, 5.4 mmol), and acetic anhydride (10 mL), and the mixture was stirred for 12 hours at 120° C. Water was poured into the resultant reaction solution to perform extraction with hexane, followed by drying with sodium sulfate. The solvent was removed from the resultant by an evaporator. The resultant was separated by column chromatography (silica gel, chloroform:hexane=2:1), to thereby obtain orange solids (1.3 g, yield: 61%).

$^1$H NMR (400 MHz, CDCl$_3$): δ7.96 (m, 2H), 7.88 (s, 1H), 7.78 (m, 3H), 7.13 (s, 1H), 2.78 (t, J=7.6 Hz, 2H), 2.59 (t, J=7.6 Hz, 2H), 1.73-1.59 (m, 4H), 1.45-1.26 (m, 12H), 0.91 (m, 6H)

(1-4) Synthesis of Exemplary Compound 1

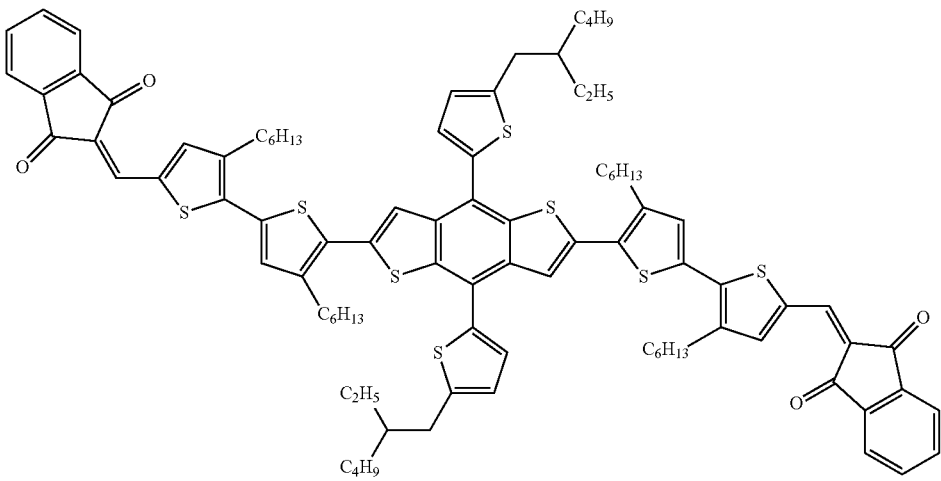

A Schlenk flask was charged with 2-((5'-bromo-3,4'-dihexyl-[2,2'-bithiophen]-5-yl)methylene)-1H-indene-1,3(2H)-dione (0.60 g, 1.1 mmol), (4,8-bis(5-(2-ethylhexyl)thiophen-2-yl)benzo[1,2-b:4,5-b']dithiophene-2,6-diyl)bis(trimethylstannane) (0.45 g, 0.5 mmol), dehydrated DMF (20 mL), and Pd(PPh$_3$)$_4$ (0.046 g, 0.04 mmol) in a nitrogen atmosphere, and the mixture was stirred for 24 hours at 85° C. Methanol was poured into the resultant reaction solution, and the precipitated solids were separated through filtration, followed by washing with ethyl acetate and acetone.

Figure 3:
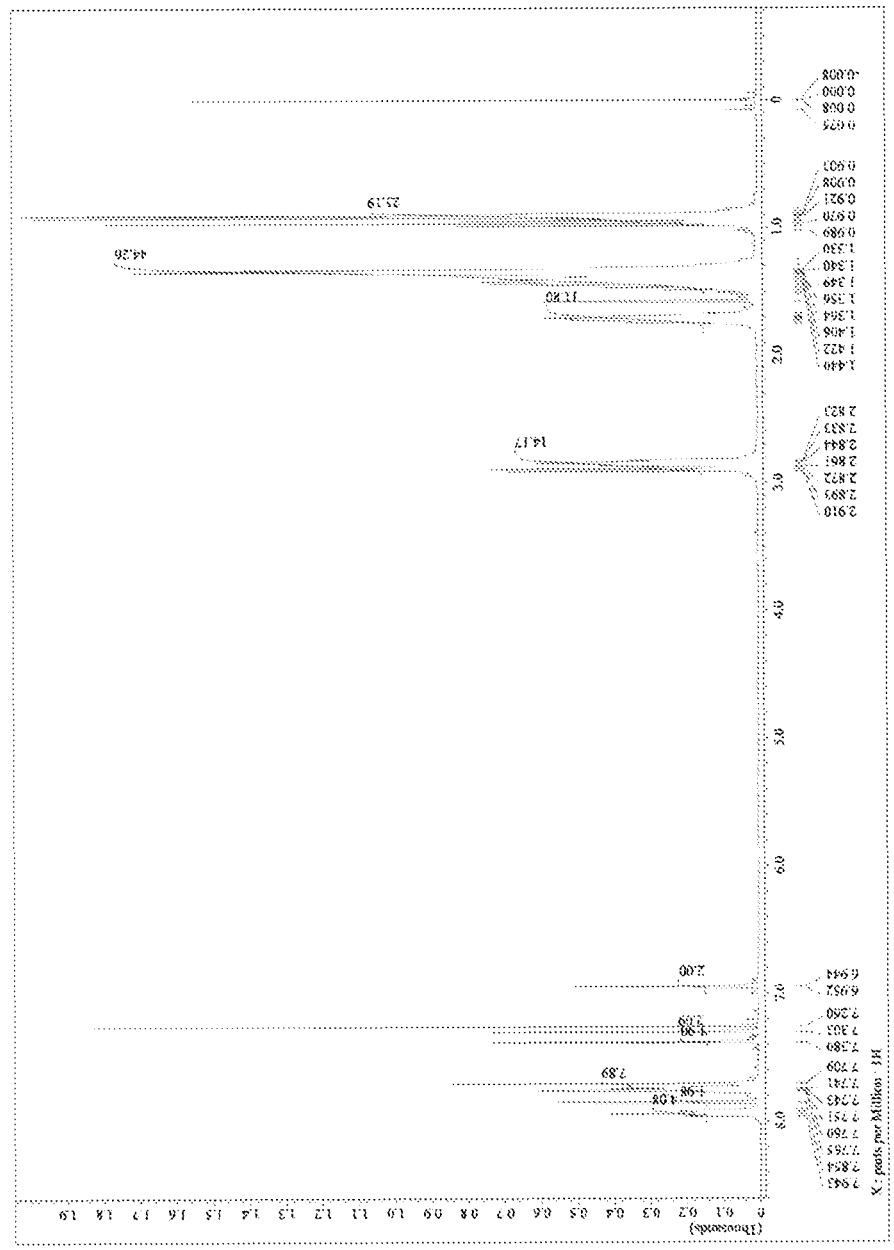
FIG. 3 is the $^1$H-NMR spectrum of the organic material of the present disclosure represented by Exemplary Compound 1 obtained in Example I-1.

The resultant was separated by column chromatography (silica gel, chloroform), to thereby obtain Exemplary Compound 1 (0.63 g, yield: 80%), which was dark purple solids. The $^1$H-NMR spectrum of Exemplary Compound 1 obtained is presented in FIG. 3.

$^1$H NMR (400 MHz, CDCl$_3$): δ8.03-7.90 (m, 4H), 7.85 (s, 2H), 7.79-7.74 (m, 6H), 7.71 (s, 2H), 7.38 (d, J=3.2 Hz, 2H), 7.30 (s, 2H), 6.95 (d, J=3.2 Hz, 2H), 2.98-2.74 (m, 12H), 1.83-1.61 (m, 10H), 1.53-1.26 (m, 40H), 1.00-0.86 (m, 24H)
$^{13}$C NMR (400 MHz, CDCl$_3$): δ190.27, 189.66, 146.04, 145.29, 144.78, 142.05, 141.87, 140.93, 140.52, 139.15, 137.00, 136.78, 136.57, 136.63, 135.63, 134.90, 134.66, 134.31, 133.62, 130.94, 127.88, 125.51, 123.86, 123.51, 122.90, 122.74, 122.00, 41.50, 34.35, 32.59, 31.64, 31.62, 30.55, 30.00, 29.65, 29.32, 29.15, 28.95, 25.76, 23.03, 22.63, 22.59, 14.10, 14.09, 14.06, 10.90

MS(MALDI-TOF): m/z 1555.59 [M]+; calcd for C$_{94}$H$_{106}$O$_4$S$_8$ 1556.07.

Example I-2

Exemplary Compound 9 below was synthesized using 2-((5'-bromo-3,4'-dihexyl-[2,2'-bithiophen]-5-yl)methylene)-1H-indene-1,3(2H)-dione obtained in Example I-1.

(2-1) Synthesis of Exemplary Compound 9

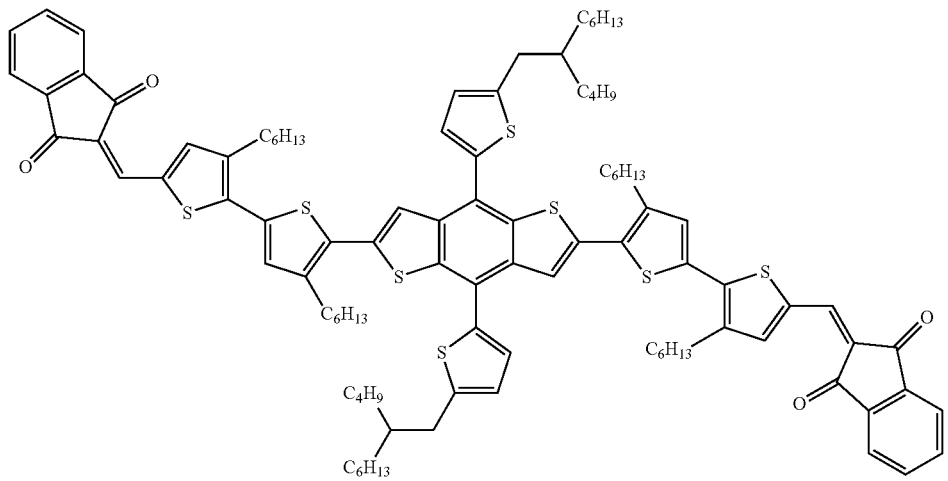

A Schlenk flask was charged with 2-((5'-bromo-3,4'-dihexyl-[2,2'-bithiophen]-5-yl)methylene)-1H-indene-1,3(2H)-dione (0.84 g, 1.5 mmol), (4,8-bis(5-(2-butyloctyl)thiophen-2-yl)benzo[1,2-b:4,5-b']dithiophene-2,6-diyl)bis(trimethylstannane) (0.71 g, 0.7 mmol), dehydrated DMF (40 mL), and Pd(PPh$_3$)$_4$ (0.032 g, 0.03 mmol) in a nitrogen atmosphere, and the mixture was stirred for 24 hours at 85° C. Methanol was poured into the resultant reaction solution, and the precipitated solids were separated by filtration, followed by washing with ethyl acetate and acetone. The resultant was separated by column chromatography (silica gel, chloroform:hexane=1:1), to thereby obtain Exemplary Compound 9 (0.85 g, yield: 72%), which was dark purple solids.

$^1$H NMR (400 MHz, CDCl$_3$): δ8.01-7.90 (m, 4H), 7.87 (s, 2H), 7.79-7.75 (m, 6H), 7.72 (s, 2H), 7.38 (d, J=3.6 Hz, 2H), 7.31 (s, 2H), 6.94 (d, J=3.6 Hz, 2H), 2.95-2.79 (m, 12H), 1.84-1.62 (m, 10H), 1.47-1.25 (m, 56H), 0.95-0.82 (m, 24H)

$^{13}$C NMR (400 MHz, CDCl$_3$): 190.28, 189.66, 146.03, 145.28, 144.78, 142.05, 141.89, 140.94, 140.53, 139.18, 137.01, 136.77, 136.56, 135.64, 134.90, 134.67, 134.33, 133.61, 130.93, 127.87, 125.52, 123.88, 123.54, 122.91, 122.74, 122.07, 40.04, 34.76, 33.48, 33.06, 31.91, 31.64, 31.62, 30.55, 30.01, 29.69, 29.63, 29.31, 29.14, 28.91, 26.67, 23.04, 22.67, 22.64, 22.59, 14.15, 14.08

MS (MALDI-TOF): m/z 1667.36 [M]+; calcd for C$_{102}$H$_{122}$O$_4$S$_8$ 1667.71

Example I-3

Exemplary Compound 6 was synthesized according to the following scheme.

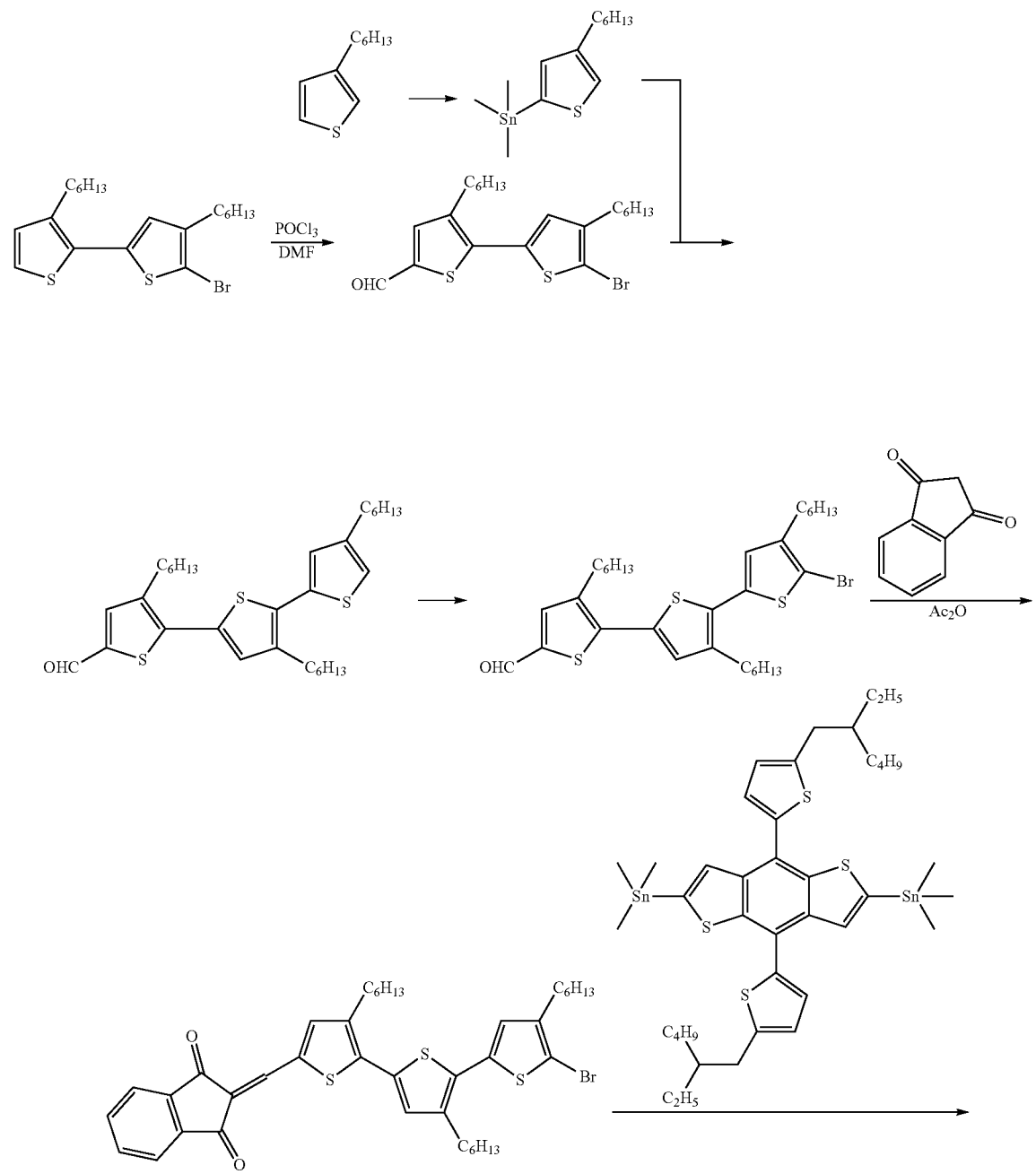

-continued

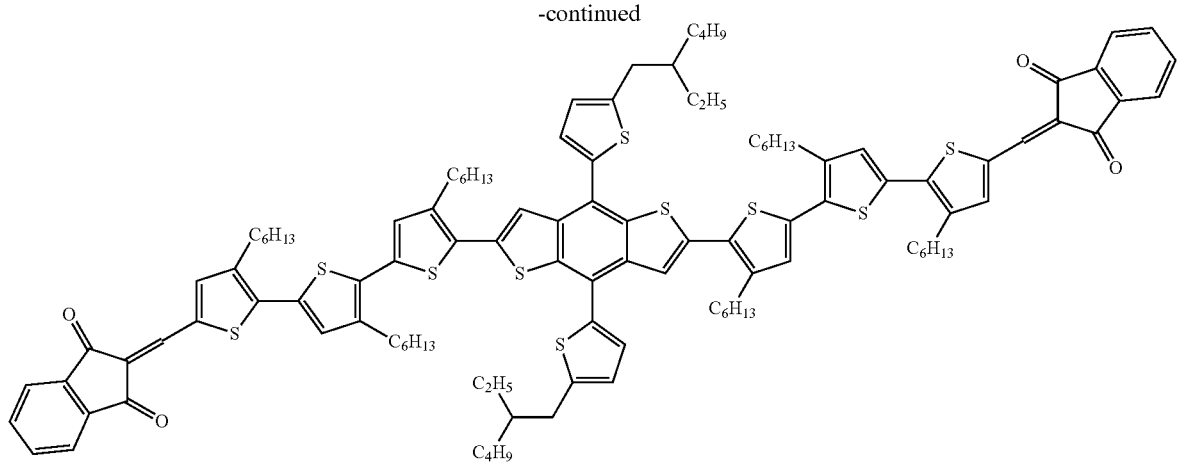

Exemplary Compound 6

(3-1) Synthesis of (4-hexylthiophen-2-yl)trimethylstannane

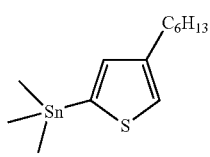

To 10 mL of dehydrated THF, diisopropylamine (4 mL, 28.5 mmol) was added at 10° C. To the mixture, 2.6 M of n-BuLi (a hexane solution) (9.88 mL, 26.2 mmol) was slowly added by dripping, and the resultant was stirred for 30 minutes at −10° C. Thereafter, a temperature of the resultant was returned to room temperature, to thereby prepare lithium diisopropylamide (LDA). To 200 mL of dehydrated THF, 3-hexylthiophene (4.03 g, 23.8 mmol) was added, and the resultant was stirred for 30 minutes at −78° C. To the resulting mixture, LDA was slowly added by dripping, and the resultant was stirred for 1 hour. To the resultant, trimethyltin chloride (5.69 g, 28.6 mmol) was slowly added, and the mixture was further stirred for 2 hours at −78° C. Thereafter, a temperature of the resultant was returned to room temperature, and the resultant was stirred for 12 hours. To the reaction container, water was added to perform extraction with hexane, the solvent was removed, and vacuum drying was performed, to thereby obtain pale yellow oil (7.92 g, yield: 100%).

$^1$H NMR (400 MHz, CDCl$_3$): δ7.19 (s, 1H), 7.01 (s, 1H), 2.64 (t, J=7.8 Hz, 2H), 1.66-1.58 (m, 2H), 1.39-1.21 (m, 6H), 0.92-0.81 (m, 3H), 0.36 (s, 9H)

(3-2) Synthesis of 5'-bromo-3,4'-dihexyl-[2,2'-bithiophene]-5-carbaldehyde

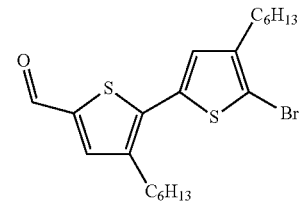

A Schlenk flask was charged with 5'-bromo-3,4'-dihexyl-2,2'-bithiophene (3.3 g, 8.0 mmol) and dehydrated DMF (25 mL) in a nitrogen atmosphere at 0° C., and the mixture was stirred. After adding POCl$_3$ (1.8 g, 12 mmol) to the mixture, the resultant mixture was stirred for 24 hours at 80° C. Water was poured into the resultant reaction solution to perform extraction with hexane, followed by drying with sodium sulfate.

The solvent was removed from the resultant by an evaporator. The resultant was separated by column chromatography (silica gel, chloroform:hexane=1:1), to thereby obtain dark yellow oil (2.0 g, yield: 57%).

$^1$H NMR (400 MHz, CDCl$_3$): δ9.82 (s, 1H), 7.57 (s, 1H), 6.96 (s, 1H), 2.74 (t, J=7.6 Hz, 2H), 2.57 (t, J=7.6 Hz, 2H), 1.70-1.57 (m, 4H), 1.44-1.23 (m, 12H), 0.96-0.83 (m, 6H)

(3-3) Synthesis of 3,4',4''-trihexyl-[2,2':5',2''-terthiophene]-5-carbaldehyde

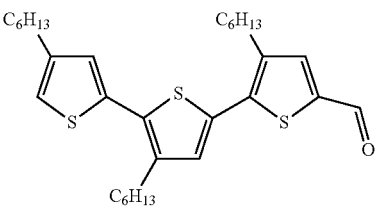

A Schlenk flask was charged with (4-hexylthiophen-2-yl)trimethylstannane (1.35 g, 4.08 mmol), 5'-bromo-3,4'-dihexyl-[2,2'-bithiophene]-5-carbaldehyde, dehydrated toluene (40 mL), and Pd(PPh$_3$)$_4$ (0.092 g, 0.08 mmol) in a nitrogen atmosphere, and the mixture was stirred for 12 hours at 100° C. Water was poured into the resultant reaction solution to perform extraction with hexane, followed by drying with sodium sulfate. The solvent was removed from the resultant by an evaporator. The resultant was separated by column chromatography (silica gel, chloroform:hexane=2:1), to thereby obtain yellow (1.80 g, yield: 84%).

$^1$H NMR (400 MHz, CDCl$_3$): δ9.82 (s, 1H), 7.58 (s, 1H), 7.11 (s, 1H), 6.99 (s, 1H), 6.94 (s, 1H), 2.83-2.74 (m, 4H), 2.64-2.60 (t, J=7.8 Hz, 2H), 1.74-1.61 (m, 6H), 1.43-1.28 (m, 18H), 0.93-0.85 (m, 9H)

(3-4) Synthesis of 5"-bromo-3,4',4"-trihexyl-[2,2':5',2"-terthiophene]-5-carbaldehyde

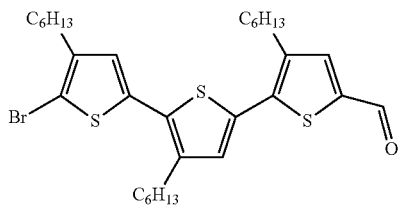

A Schlenk flask was charged with 3,4',4"-trihexyl-[2,2':5',2"-terthiophene]-5-carbaldehyde (1.60 g, 3.03 mmol) and dehydrated DMF (40 mL) in a nitrogen atmosphere at 0° C., and the mixture was stirred. After slowly adding NBS (0.54 g, 3.03 mmol) to the mixture, the resultant mixture was stirred for 2 hours.

Water was poured into the resultant reaction solution to perform extraction with hexane, followed by drying with sodium sulfate. The solvent was removed from the resultant by an evaporator. The resultant was separated by column chromatography (silica gel, chloroform:hexane=2:1), to thereby obtain dark yellow oil (1.65 g, yield: 89%).

$^1$H NMR (400 MHz, CDCl$_3$): δ9.83 (s, 1H), 7.59 (s, 1H), 7.10 (s, 1H), 6.85 (s, 1H), 2.82-2.78 (t, J=7.8 Hz, 2H), 2.74-2.70 (t, J=7.8 Hz, 2H), 2.59-2.52 (m, J=7.8 Hz, 2H), 1.71-1.57 (m, 6H), 1.45-1.22 (m, 18H), 0.95-0.84 (m, 9H)

(3-5) Synthesis of 2-((5"-bromo-3,4',4"-trihexyl-[2,2':5',2"-terthiophen]-5-yl)methylene)-1H-indene-1,3(2H)-dione

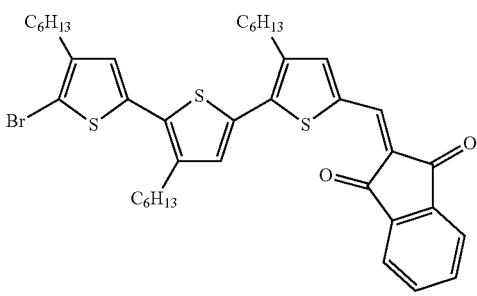

A Schlenk flask was charged with 5"-bromo-3,4',4"-trihexyl-[2,2':5',2"-terthiophene]-5-carbaldehyde (1.45 g, 2.38 mmol), 1H-indene-1,3(2H)-dione (0.70 g, 4.76 mmol), and acetic anhydride (10 mL) in a nitrogen atmosphere, and the mixture was stirred for 12 hours at 120° C. Water was poured into the resultant reaction solution to perform extraction with hexane, followed by drying with sodium sulfate. The solvent was removed from the resultant by an evaporator. The resultant was separated by column chromatography (silica gel, chloroform:hexane=2:1), to thereby obtain dark green solids (1.40 g, yield: 80%).

$^1$H NMR (400 MHz, CDCl$_3$): δ7.99-7.94 (m, 2H), 7.89 (s, 1H), 7.82-7.76 (m, 3H), 7.28 (s, 1H), 6.88 (s, 1H), 2.86-2.82 (t, J=7.8 Hz, 2H), 2.76-2.72 (t, J=7.8 Hz, 2H), 2.60-2.56 (t, J=7.8 Hz, 2H), 1.75-1.61 (m, 6H), 1.44-1.25 (m, 18H), 0.97-0.86 (m, 9H)

(3-6) Synthesis of Exemplary Compound 6

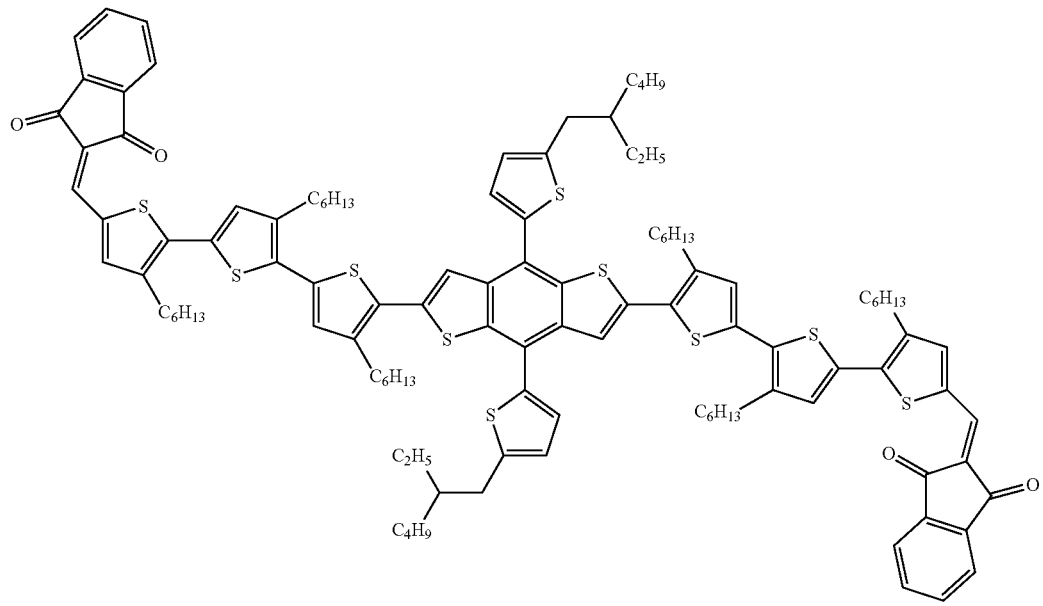

A Schlenk flask was charged with 2-((5"-bromo-3',4'"-trihexyl-[2,2':5',2"-terthiophen]-5-yl)methylene)-1H-indene-1,3(2H)-dione (0.60 g, 1.4 mmol), (4,8-bis(5-(2-ethylhexyl)thiophen-2-yl)benzo[1,2-b:4,5-b']dithiophene-2,6-diyl)bis(trimethylstannane) (0.45 g, 0.66 mmol), dehydrated DMF (20 mL), and Pd(PPh$_3$)$_4$ (0.031 g, 0.03 mmol) in a nitrogen atmosphere, and the mixture was stirred for 24 hours at 85° C.

Methanol was poured into the resultant reaction solution, and the precipitated solids were separated by filtration, followed by washing with ethyl acetate and acetone. The resultant was separated by column chromatography (silica gel, chloroform), to thereby obtain Exemplary Compound 6 (0.66 g, yield: 53%), which was dark purple solids.

$^1$H NMR (400 MHz, CDCl$_3$): δ7.98-7.94 (m, 4H), 7.88 (s, 2H), 7.80-7.76 (m, 6H), 7.69 (s, 2H), 7.38-7.37 (d, J=3.2 Hz, H), 7.31 (s, 2H), 7.06 (s, 2H), 6.93-6.92 (d, J=3.2 Hz, 2H), 2.93-2.77 (m, 16H), 1.80-1.67 (m, 14H), 1.49-1.31 (m, 52H), 1.00-0.88 (m, 30H)

MS(MALDI-TOF): m/z 1887.75 [M]+; calcd for C$_{114}$H$_{134}$O$_4$S$_{10}$ 1887.39.

Example II-1

(Production of Electron-Transporting Layer)

Zinc acetate (available from Sigma-Aldrich Co., LLC) in an amount of 1 g, 0.28 g of ethanolamine (available from Sigma-Aldrich Co., LLC), and 10 mL of methoxyethanol (available from Wako Pure Chemical Industries, Ltd.) were stirred overnight at room temperature to thereby prepare a zinc oxide precursor solution. The zinc oxide precursor solution was applied onto an ITO substrate by spin coating in a manner that a film thickness was to be 20 nm, and the applied solution was dried for 10 minutes at 200° C., to thereby form an electron-transporting layer.

(Production of Photoelectric Conversion Layer)

In 1 mL of chloroform, 7.5 mg of Exemplary Compound 1 and 7.5 mg of PC71BM (available from Frontier Carbon Corporation) were dissolved to prepare a photoelectric conversion layer solution. Onto the above-described electron-transporting layer, the photoelectric conversion layer solution was applied by spin coating in a manner that a film thickness was to be 100 nm, to thereby form a photoelectric conversion layer.

(Production of Hole-Transporting Layer and Metal Electrode)

On the photoelectric conversion layer, molybdenum oxide (available from KOJUNDO CHEMICAL LABORATORY CO., LTD.) in the thickness of 20 nm, and silver in the thickness of 100 nm were sequentially formed by vacuum vapor deposition, to thereby produce a photoelectric conversion element.

Conversion efficiency of the obtained photoelectric conversion element under irradiation of white LED (0.07 mW/cm$^2$) was measured.

The measurement was performed by using a desk lamp CDS-90a available from Cosmotechno Co., Ltd. as the white LED, and a solar battery evaluation system As-510-PV03 available from NF Corporation as the evaluation device. The output of the LED light source was measured by means of a color meter C-7000 available from SEKONIC CORPORATION. The result is presented in Table 1.

Example II-2

A photoelectric conversion element was produced and evaluated in the same manner as in Example II-1, except that Exemplary Compound 1 was replaced with Exemplary Compound 9. The result is presented in Table 1.

Example II-3

A photoelectric conversion element was produced and evaluated in the same manner as in Example II-1, except that Exemplary Compound 1 was replaced with Exemplary Compound 11. The result is presented in Table 1.

Example II-4

A photoelectric conversion element was produced and evaluated in the same manner as in Example II-1, except that PC71BM was replaced with a fullerene derivative represented by Structural Formula A below. The result is presented in Table 1.

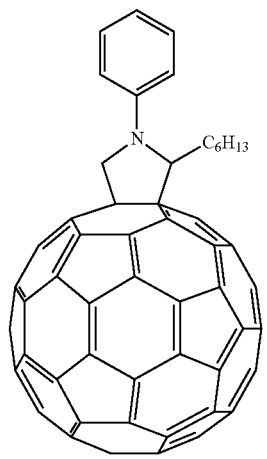

Structural Formula A

Example II-5

A photoelectric conversion element was produced and evaluated in the same manner as in Example 11-2, except that PC71BM was replaced with a fullerene derivative represented by Structural Formula A above. The result is presented in Table 1.

Example II-6

A photoelectric conversion element was produced and evaluated in the same manner as in Example 11-3, except that PC71BM was replaced with a fullerene derivative represented by Structural Formula A above. The result is presented in Table 1.

Example II-7

A photoelectric conversion element was produced and evaluated in the same manner as in Example 11-4, except that the fullerene derivative represented by Structural Formula A was replaced with a fullerene derivative represented by Structural Formula B below. The result is presented in Table 1.

Structural Formula B

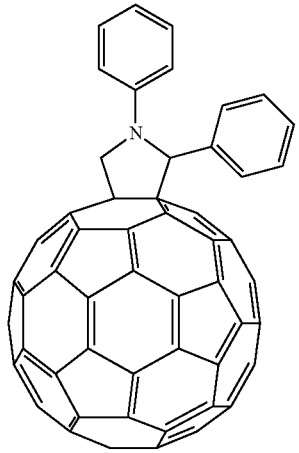

Example II-8

A photoelectric conversion element was produced and evaluated in the same manner as in Example 11-5, except that the fullerene derivative represented by Structural Formula A was replaced with a fullerene derivative represented by Structural Formula B. The result is presented in Table 1.

Example II-9

A photoelectric conversion element was produced and evaluated in the same manner as in Example 11-6, except that the fullerene derivative represented by Structural Formula A was replaced with a fullerene derivative represented by Structural Formula B. The result is presented in Table 1.

Example II-10

A photoelectric conversion element was produced and evaluated in the same manner as in Example 11-7, except that the production of the electron-transporting layer was changed as described below. The result is presented in Table 1.

(Production of Electron-Transporting Layer)

Zinc acetate (available from Sigma-Aldrich Co., LLC) in an amount of 1 g, 0.28 g of ethanolamine (available from Sigma-Aldrich Co., LLC), and 10 mL of methoxyethanol (available from Wako Pure Chemical Industries, Ltd.) were stirred overnight at room temperature to thereby prepare a zinc oxide precursor solution. The zinc oxide precursor solution was applied onto an ITO substrate by spin coating in a manner that a film thickness was to be 20 nm, and the applied solution was dried for 10 minutes at 200° C. Onto the resultant film, a dimethylaminobenzoic acid ethanol solution (1 mg/mL) was applied by spin coating at 5,000 rpm, to thereby form an electron-transporting layer.

Example II-11

A photoelectric conversion element was produced and evaluated in the same manner as in Example 11-8, except that the production of the electron-transporting layer was changed to the production of the electron-transporting layer in Example II-10. The result is presented in Table 1.

Example II-12

A photoelectric conversion element was produced and evaluated in the same manner as in Example 11-9, except that the production of the electron-transporting layer was changed to the production of the electron-transporting layer in Example II-10. The result is presented in Table 1.

Comparative Example 1

A photoelectric conversion element was produced and evaluated in the same manner as in Example 11-7, except that Exemplary Compound 1 was replaced with Comparative Compound 1 disclosed in "Chem. Mater. 2013, 25, 2274-2281." Comparative Compound 1 was synthesized according to the method described in "Chem. Mater. 2013, 25, 2274-2281." The result is presented in Table 1.

Comparative Compound 1

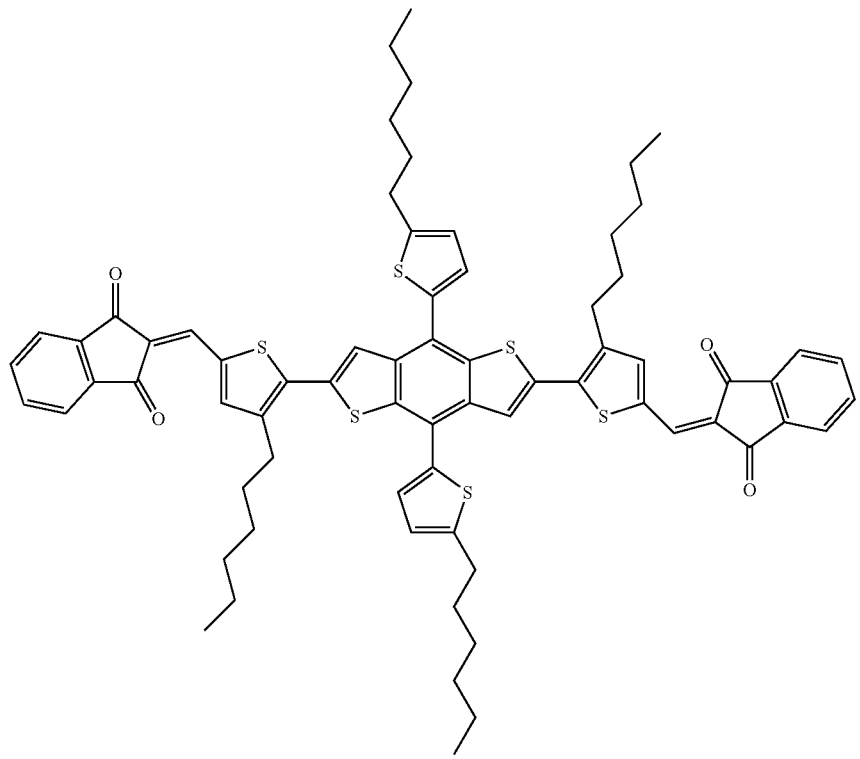

Comparative Example 2

A photoelectric conversion element was produced and evaluated in the same manner as in Example 11-7, except that Exemplary Compound 1 was replaced with Comparative Compound 2 disclosed in "Chem. Mater. 2013, 25, 2274-2281." Comparative Compound 2 was synthesized according to the method described in "Chem. Mater. 2013, 25, 2274-2281." The result is presented in Table 1.

Comparative Compound 2

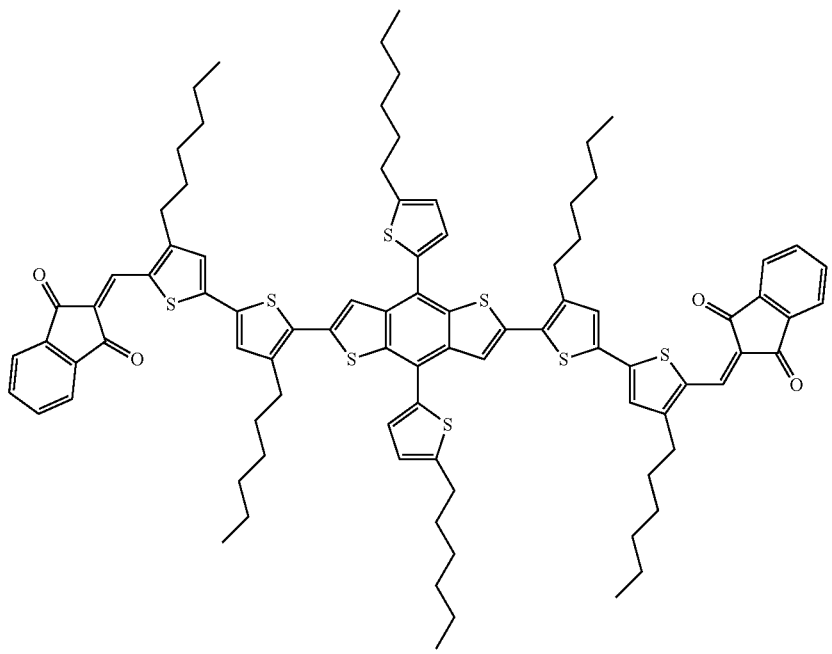

Comparative Example 3

A photoelectric conversion element was produced and evaluated in the same manner as in Comparative Example 1, except that the electron-transporting layer was changed to the electron-transporting layer of Example II-10. The result is presented in Table 1.

Comparative Example 4

A photoelectric conversion element was produced and evaluated in the same manner as in Comparative Example 2, except that the electron-transporting layer was changed to the electron-transporting layer of Example II-10. The result is presented in Table 1.

Comparative Example 5

A photoelectric conversion element was produced in the same manner as in Example II-1, except that Exemplary Compound 1 was replaced with 6 mg of PTB7 (Poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]], available from 1-Material), the amount of PC71BM was changed to 9 mg, 1 vol % of 1,8-diiodooctane was further added, and the solvent was changed to chlorobenzene. The result is presented in Table 1.

Comparative Example 6

A photoelectric conversion element was produced and evaluated in the same manner as in Comparative Example 5, except that the electron-transporting layer was changed to the electron-transporting layer of Example II-10. The result is presented in Table 1.

Comparative Example 7

An amorphous silicon solar cell AM-1801 available from Panasonic Corporation was evaluated by the measuring method described in Example II-1. The result is presented in Table 1.

Moreover, the photoelectric conversion elements produced in Examples II-1 to II-12 and the photoelectric conversion elements produced in Comparative Examples 1 to 6 were each sealed, followed by performing a storage test at 85° C. for 100 hours. The solar cell used in Comparative Example 7 was also subjected to the storage test in the same manner. Conversion efficiency of each photoelectric conversion element or the solar cell after the storage test at 85° C. for 100 hours was measured, and a retention rate relative to the initial conversion efficiency was calculated. The results are presented in Table 1.

TABLE 1

|  | Initial conversion efficiency | Conversion efficiency retention rate after storage of 85° C., 100 h |
| --- | --- | --- |
| Ex. II-1 | 9.1% | 65% |
| Ex. II-2 | 9.5% | 69% |
| Ex. II-3 | 9.0% | 73% |
| Ex. II-4 | 10.6% | 69% |
| Ex. II-5 | 11.2% | 71% |
| Ex. II-6 | 10.4% | 71% |
| Ex. II-7 | 13.4% | 70% |
| Ex. II-8 | 13.9% | 65% |
| Ex. II-9 | 14.1% | 69% |
| Ex. II-10 | 17.8% | 68% |
| Ex. II-11 | 16.9% | 81% |
| Ex. II-12 | 17.1% | 79% |
| Comp. Ex. 1 | 6.5% | 83% |
| Comp. Ex. 2 | 7.8% | 41% |
| Comp. Ex. 3 | 7.2% | 45% |
| Comp. Ex. 4 | 7.8% | 50% |
| Comp. Ex. 5 | 7.9% | 51% |
| Comp. Ex. 6 | 7.4% | 21% |
| Comp. Ex. 7 | 8.3% | 25% |

As described above, the photoelectric conversion elements produced using the organic material of the present disclosure had high conversion efficiency against weak light of 0.07 mW/cm$^2$ and were excellent compared to the photoelectric conversion elements of Comparative Examples.

Moreover, the photoelectric conversion elements produced using the organic material of the present disclosure had high heat resistance, and were excellent in terms of durability compared to the photoelectric conversion elements of Comparative Examples.

For example, embodiments of the present disclosure are as follows.

<1> An organic material represented by General Formula (1) below:

General Formula (1)

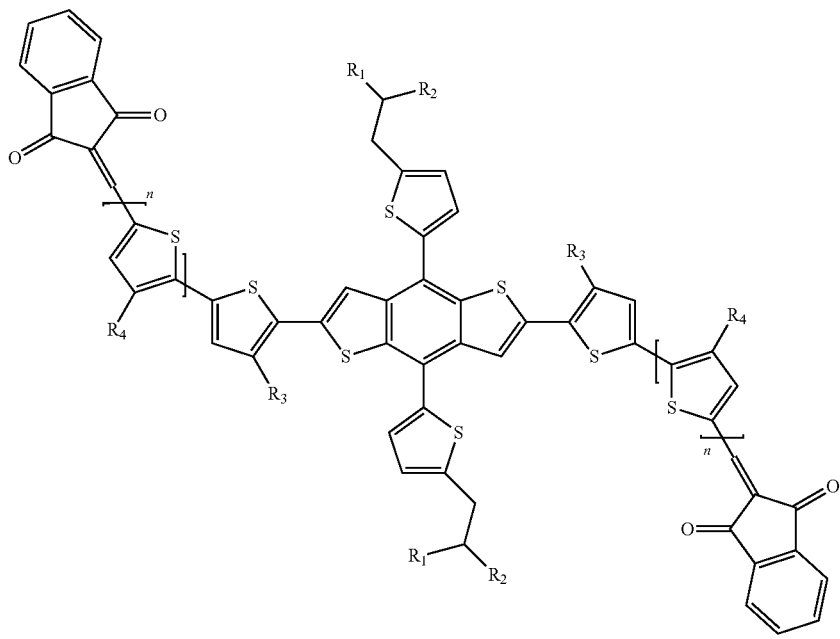

where, in General Formula (1), $R_1$ and $R_2$ are each independently an alkyl group having from 2 through 8 carbon atoms, $R_3$ and $R_4$ are each independently a straight-chain alkyl group having 1, 2, 4, 6, or 12 carbon atoms, or a hydrogen atom, and n is an integer of 1 or 2.

<2> The organic material according to <1>, wherein the organic material is represented by General Formula (2) below:

General Formula (2)

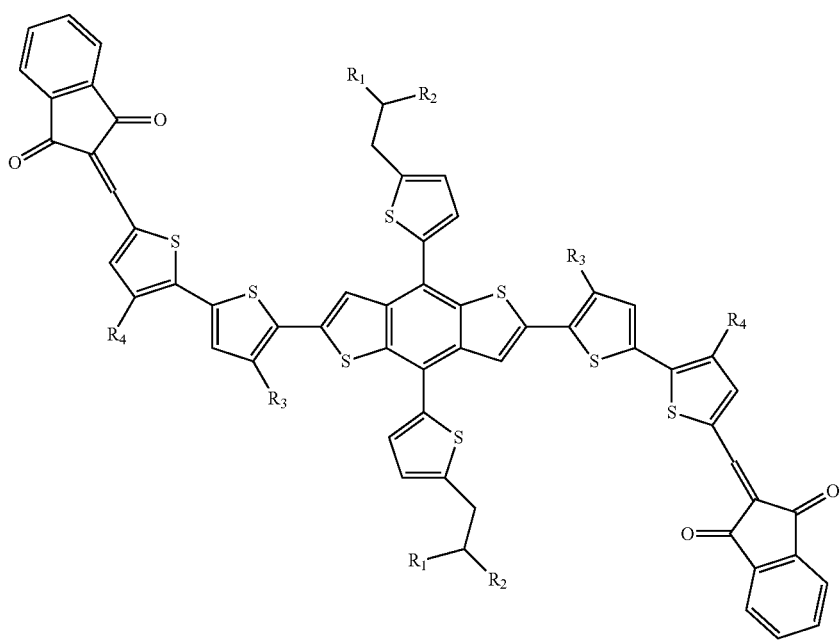

where, in General Formula (2), $R_1$ and $R_2$ are each independently an alkyl group having from 2 through 8 carbon atoms, and $R_3$ and $R_4$ are each independently a straight-chain alkyl group having 1, 2, 4, 6, or 12 carbon atoms, or a hydrogen atom.

<3> The organic material according to <1>, wherein the organic material is represented by General Formula (3) below:

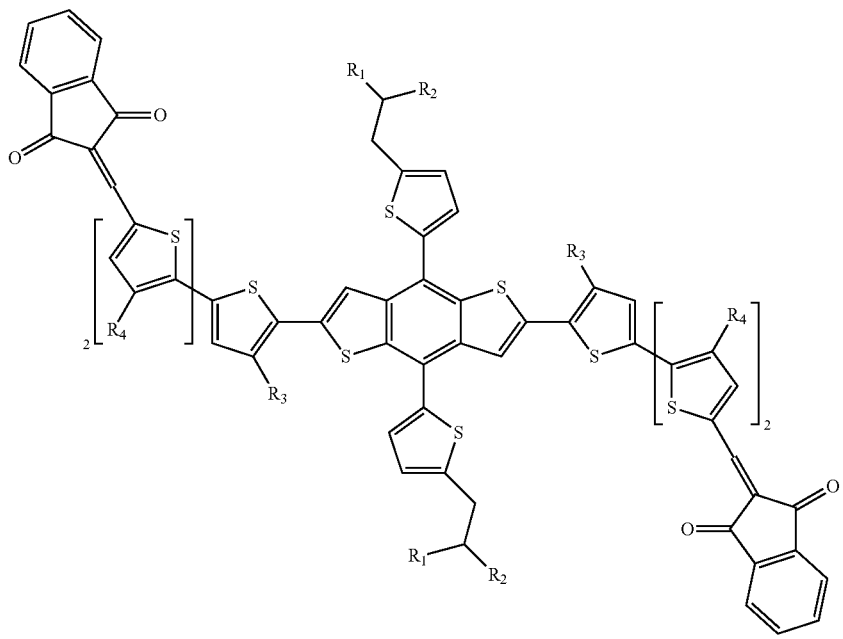

General Formula (3)

where, in General Formula (3), $R_1$ and $R_2$ are each independently an alkyl group having from 2 through 8 carbon atoms, and $R_3$ and $R_4$ are each independently a straight-chain alkyl group having 1, 2, 4, 6, or 12 carbon atoms, or a hydrogen atom.

<4> A photoelectric conversion element including:
a substrate;
a first electrode;
an electron-transporting layer;
a photoelectric conversion layer;
a hole-transporting layer; and
a second electrode, where the first electrode, the electron-transporting layer, the photoelectric conversion layer, the hole-transporting layer, and the second electrode are disposed on the substrate,
wherein the photoelectric conversion layer includes the organic material according to any one of <1> to <3> and an n-type semiconductor material.

<5> The photoelectric conversion element according to <4>, wherein the n-type semiconductor material included in the photoelectric conversion layer is a fullerene derivative.

<6> The photoelectric conversion element according to <5>, wherein the fullerene derivative is a compound represented by General Formula (4) below:

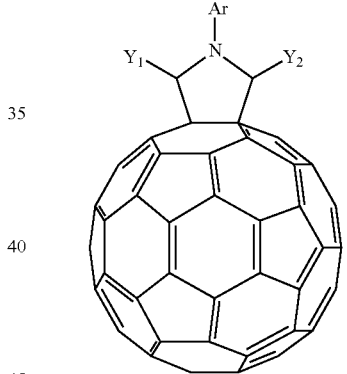

General Formula (4)

where, in General Formula (4), $Y_1$ and $Y_2$ are each independently a hydrogen atom, an alkyl group, an alkenyl group, an alkynyl group, an aryl group, or an aralkyl group with the proviso that both $Y_1$ and $Y_2$ are not hydrogen atoms at the same time, Ar is an aryl group, and in General Formula (4), a site represented by:

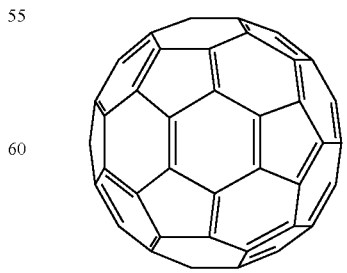

is a fullerene skeleton having 60 carbon atoms.

<7> The photoelectric conversion element according to <5> or <6>, wherein the fullerene derivative is a compound represented by General Formula (5) below:

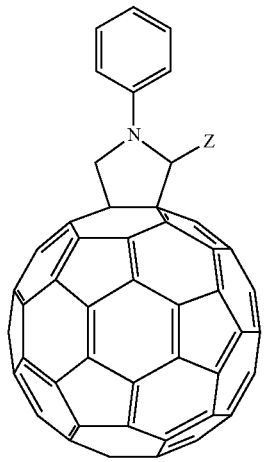

General Formula (5)

where, in General Formula (5), Z is a phenyl group, a 1-naphthyl group, or a 2-naphthyl group.

<8> The photoelectric conversion element according to any one of <4> to <7>,
wherein the electron-transporting layer includes a first layer including metal oxide, and a second layer disposed between the first layer and the photoelectric conversion layer, the second layer including an amine compound represented by General Formula (6) below:

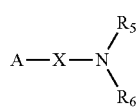

General Formula (6)

where, in General Formula (6), $R_5$ and $R_6$ are each independently an alkyl group having from 1 through 4 carbon atoms, where $R_5$ and $R_6$ may be bonded to each other to form a ring, X is a bivalent aromatic group having from 6 through 14 carbon atoms or an alkylene group having from 1 through 4 carbon atoms, and A is any one of substituents below:

—COOH

—P(=O)(OH)$_2$

—Si(OH)$_3$

The organic material according to any one of <1> to <3>, and the photoelectric conversion element according to any one of <4> to <8> can solve the above-described various problems existing in the art, and achieve the object of the present disclosure.

What is claimed is:

1. An organic material represented by General Formula (1) below:

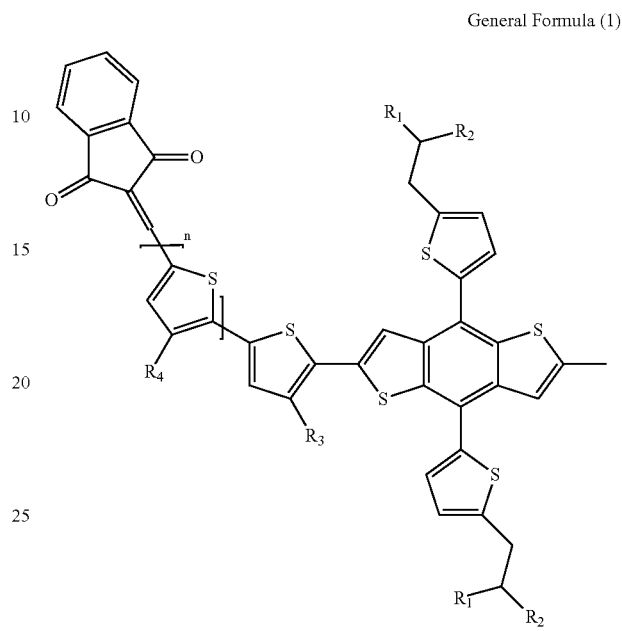

General Formula (1)

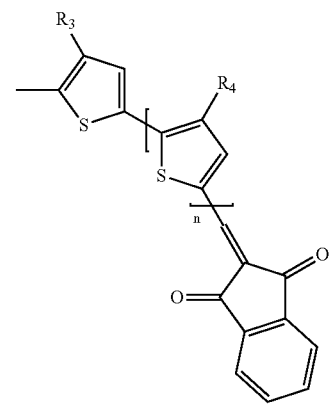

where, in General Formula (1), $R_1$ and $R_2$ are each independently an alkyl group having from 2 through 8 carbon atoms, $R_3$ and $R_4$ are each independently a straight-chain alkyl group having 1, 2, 4, 6, or 12 carbon atoms, or a hydrogen atom, and n is an integer of 1 or 2.

2. The organic material according to claim 1,
wherein the organic material is represented by General Formula (2) below:

General Formula (2)

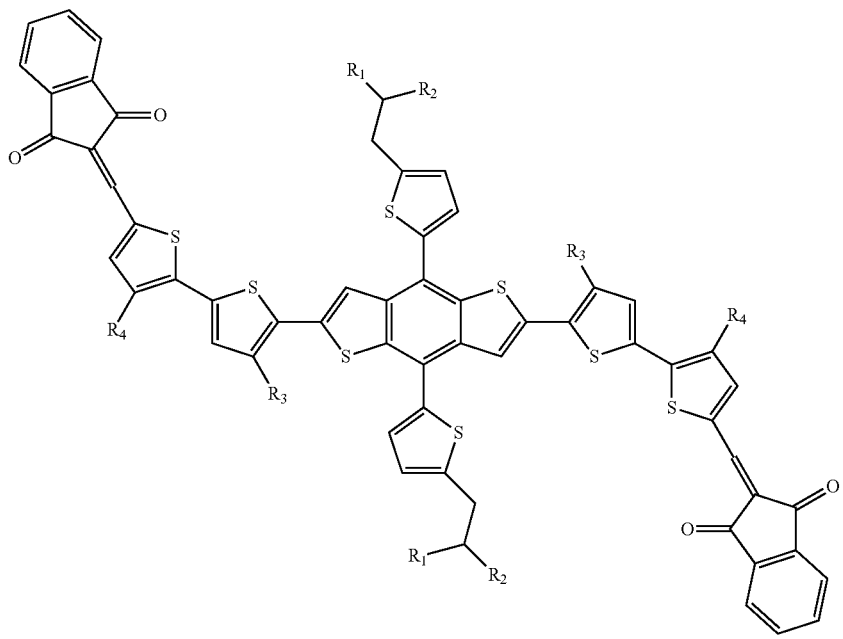

where, in General Formula (2), $R_1$ and $R_2$ are each independently an alkyl group having from 2 through 8 carbon atoms, and $R_3$ and $R_4$ are each independently a straight-chain alkyl group having 1, 2, 4, 6, or 12 carbon atoms, or a hydrogen atom.

3. The organic material according to claim 1, wherein the organic material is represented by General Formula (3) below:

General Formula (3)

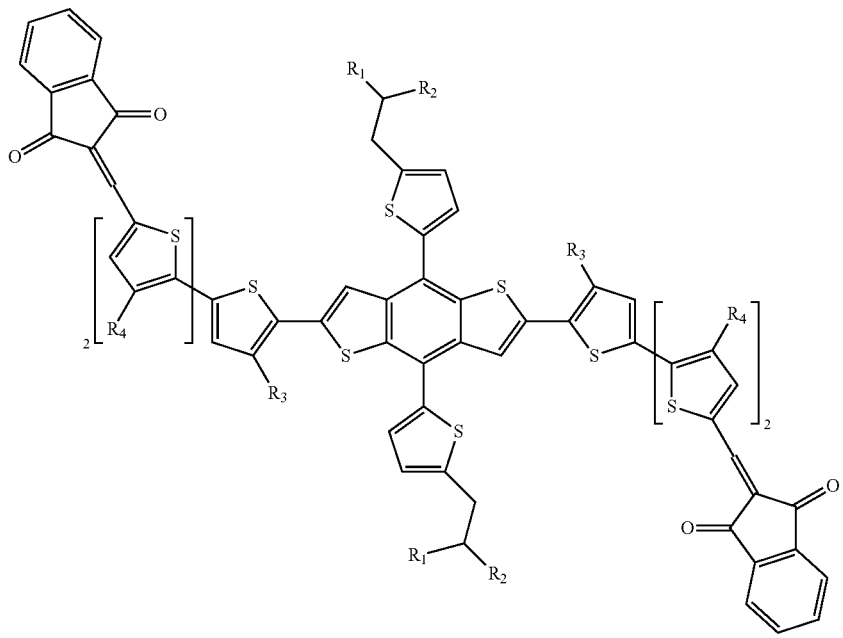

where, in General Formula (3), $R_1$ and $R_2$ are each independently an alkyl group having from 2 through 8 carbon atoms, and $R_3$ and $R_4$ are each independently a straight-chain alkyl group having 1, 2, 4, 6, or 12 carbon atoms, or a hydrogen atom.

4. A photoelectric conversion element comprising:
a substrate;
a first electrode;
an electron-transporting layer;
a photoelectric conversion layer;
a hole-transporting layer; and
a second electrode, where the first electrode, the electron-transporting layer, the photoelectric conversion layer, the hole-transporting layer, and the second electrode are disposed on the substrate,
wherein the photoelectric conversion layer includes an organic material represented by General Formula (1) below, and an n-type semiconductor material,

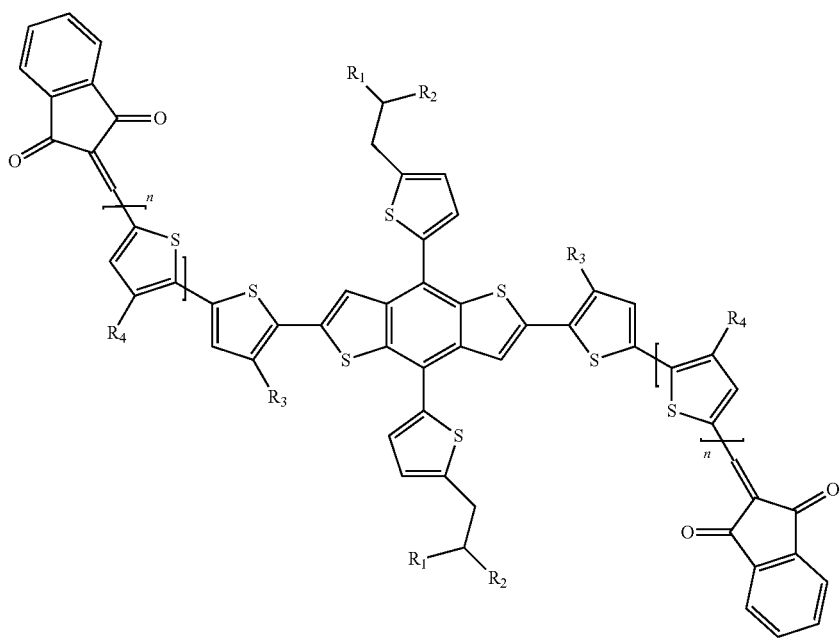

General Formula (1)

where, in General Formula (1), $R_1$ and $R_2$ are each independently an alkyl group having from 2 through 8 carbon atoms, $R_3$ and $R_4$ are each independently a straight-chain alkyl group having 1, 2, 4, 6, or 12 carbon atoms, or a hydrogen atom, and n is an integer of 1 or 2.

5. The photoelectric conversion element according to claim 4, wherein the n-type semiconductor material included in the photoelectric conversion layer is a fullerene derivative, and wherein the fullerene derivative is a compound represented by General Formula (4) below:

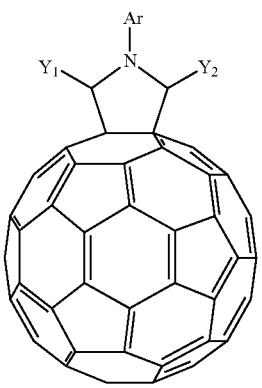

General Formula (4)

where, in General Formula (4), $Y_1$ and $Y_2$ are each independently a hydrogen atom, an alkyl group, an alkenyl group, an alkynyl group, an aryl group, or an aralkyl group with the proviso that both $Y_1$ and $Y_2$ are not hydrogen atoms at the same time, Ar is an aryl group, and in General Formula (4), a site represented by:

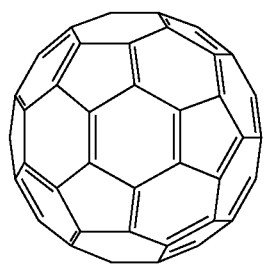

is a fullerene skeleton having 60 carbon atoms.

6. The photoelectric conversion element according to claim 4, wherein the n-type semiconductor material included in the photoelectric conversion layer is a fullerene derivative, and wherein the fullerene derivative is a compound represented by General Formula (5) below:

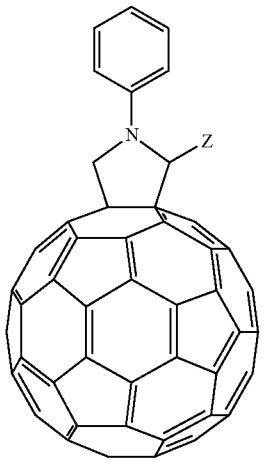

General Formula (5)

where, in General Formula (5), Z is a phenyl group, a 1-naphthyl group, or a 2-naphthyl group.

7. The photoelectric conversion element according to claim 4, wherein the electron-transporting layer includes a first layer including metal oxide, and a second layer disposed between the first layer and the photoelectric conversion layer, the second layer including an amine compound represented by General Formula (6) below:

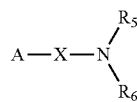

General Formula (6)

where, in General Formula (6), $R_5$ and $R_6$ are each independently an alkyl group having from 1 through 4 carbon atoms, where $R_5$ and $R_6$ may be bonded to each other to form a ring, X is a bivalent aromatic group having is from 6 through 14 carbon atoms or an alkylene group having from 1 through 4 carbon atoms, and A is any one of substituents below:

—COOH

—P(=O)(OH)$_2$

—Si(OH)$_3$.

* * * * *